(12) United States Patent
Giridhar et al.

(10) Patent No.: US 11,547,675 B2
(45) Date of Patent: Jan. 10, 2023

(54) METHODS AND SYSTEMS FOR DEPOSITING ACTIVE INGREDIENTS ON SUBSTRATES

(71) Applicant: Purdue Research Foundation, West Lafayette, IN (US)

(72) Inventors: Arun V. Giridhar, West Lafayette, IN (US); Michael Harris, West Lafayette, IN (US); Gintaras V. Reklaitis, West Lafayette, IN (US); Lynne S. Taylor, West Lafayette, IN (US); Zoltan K. Nagy, West Lafayette, IN (US); Elcin Icten, West Lafayette, IN (US); Frederick Fiesser, Philadelphia, PA (US); Laura Hirshfield, Ann Arbor, MI (US)

(73) Assignee: Purdue Research Foundation, West Lafayette, IN (US)

( * ) Notice: Subject to any disclaimer, the term of this patent is extended or adjusted under 35 U.S.C. 154(b) by 24 days.

Patent file contains an affidavit/declaration under 37 CFR 1.130(b).

(21) Appl. No.: 15/751,771

(22) PCT Filed: Aug. 9, 2016

(86) PCT No.: PCT/US2016/046217
§ 371 (c)(1),
(2) Date: Feb. 9, 2018

(87) PCT Pub. No.: WO2017/027528
PCT Pub. Date: Feb. 16, 2017

(65) Prior Publication Data
US 2018/0228737 A1    Aug. 16, 2018

Related U.S. Application Data

(60) Provisional application No. 62/203,013, filed on Aug. 10, 2015.

(51) Int. Cl.
*A61K 9/70* (2006.01)
*A61K 47/10* (2017.01)
(Continued)

(52) U.S. Cl.
CPC .......... *A61K 9/7007* (2013.01); *A61K 31/167* (2013.01); *A61K 31/192* (2013.01);
(Continued)

(58) Field of Classification Search
CPC ....... B05B 17/0615; B05B 1/08; H01L 31/00; B05D 5/00; C12Q 1/70; A61K 31/015; A61K 9/22; A61K 31/495
See application file for complete search history.

(56) References Cited

U.S. PATENT DOCUMENTS 4,551,073 A * 11/1985 Schwab .................... F04C 2/22
                                                            417/352
5,277,927 A *  1/1994 Burns ................... B05B 12/082
                                                              427/8
(Continued)

FOREIGN PATENT DOCUMENTS

WO    2014/085725    6/2014

OTHER PUBLICATIONS

Hirshfield et al., Dropwise Additive Manufacturing of Pharmaceutical Products for Solvent-Based Dosage Forms, 2013 Journal of Pharmaceutical Sciences, vol. 103, pp. 496-506 . (Year: 2013).*

(Continued)

*Primary Examiner* — Dah-Wei D. Yuan
*Assistant Examiner* — Andrew J Bowman
(74) *Attorney, Agent, or Firm* — Reichel Stohry Dean LLP; Natalie J. Dean; Mark C. Reichel

(57) ABSTRACT

Systems and methods for delivering active ingredients, such as pharmaceutically active ingredients, to substrates are described herein. The active ingredients are delivered as (Continued)

fluids to a fluid-dispensing device for the creation of one or more drops for deposition onto substrates such as for the creation of microdoses. The invention further includes microdoses made by such processes.

18 Claims, 13 Drawing Sheets

(51) Int. Cl.
*A61K 31/415* (2006.01)
*A61K 31/167* (2006.01)
*A61K 31/192* (2006.01)
*A61K 31/196* (2006.01)
*A61K 31/635* (2006.01)
*A61K 47/14* (2017.01)
*A61K 47/34* (2017.01)
*A61K 47/38* (2006.01)
*B01J 4/00* (2006.01)
*B01J 4/02* (2006.01)

(52) U.S. Cl.
CPC .......... *A61K 31/196* (2013.01); *A61K 31/415* (2013.01); *A61K 31/635* (2013.01); *A61K 47/10* (2013.01); *A61K 47/14* (2013.01); *A61K 47/34* (2013.01); *A61K 47/38* (2013.01); *B01J 4/002* (2013.01); *B01J 4/008* (2013.01); *B01J 4/02* (2013.01); *B01J 2204/005* (2013.01); *B01J 2204/007* (2013.01)

(56) References Cited

U.S. PATENT DOCUMENTS

| | | | | |
|---|---|---|---|---|
| 5,453,447 | A * | 9/1995 | End | A61K 9/0019 514/763 |
| 5,618,559 | A * | 4/1997 | Desai | A61P 31/04 424/468 |
| 6,413,965 | B1 * | 7/2002 | Mylari | A61P 3/00 514/255.05 |
| 7,413,690 | B1 | 8/2008 | Cheboyina et al. | |
| 2004/0112978 | A1 * | 6/2004 | Reichel | B01L 3/0268 239/71 |
| 2007/0077309 | A1 | 4/2007 | Wong | |
| 2008/0286751 | A1 * | 11/2008 | Renaud | B01L 3/0268 435/5 |
| 2009/0301550 | A1 * | 12/2009 | Hunt | B41J 2/04505 136/252 |
| 2014/0263724 | A1 * | 9/2014 | Ovchinnikov | B05B 17/0615 239/102.2 |

OTHER PUBLICATIONS

Hirshfield et al., Rising Damp, 2015, The Medicine Maker, https://themedicinemaker.com/discovery-development/rising-dampp (Year: 2015).*

International Searching Authority, International Search Report, PCT/US2016/046217, dated Jan. 6, 2017.

International Searching Authority, Written Opinion of the International Searching Authority, PCT/US2016/046217, dated Jan. 6, 2017.

Hirshfield, Laura et al, "Dropwise additive manufacturing of pharmaceutical products for solvent-based dosage forms," J Pharm Sci, Feb. 2014, vol. 103, issue 2, pp. 496-506.

* cited by examiner

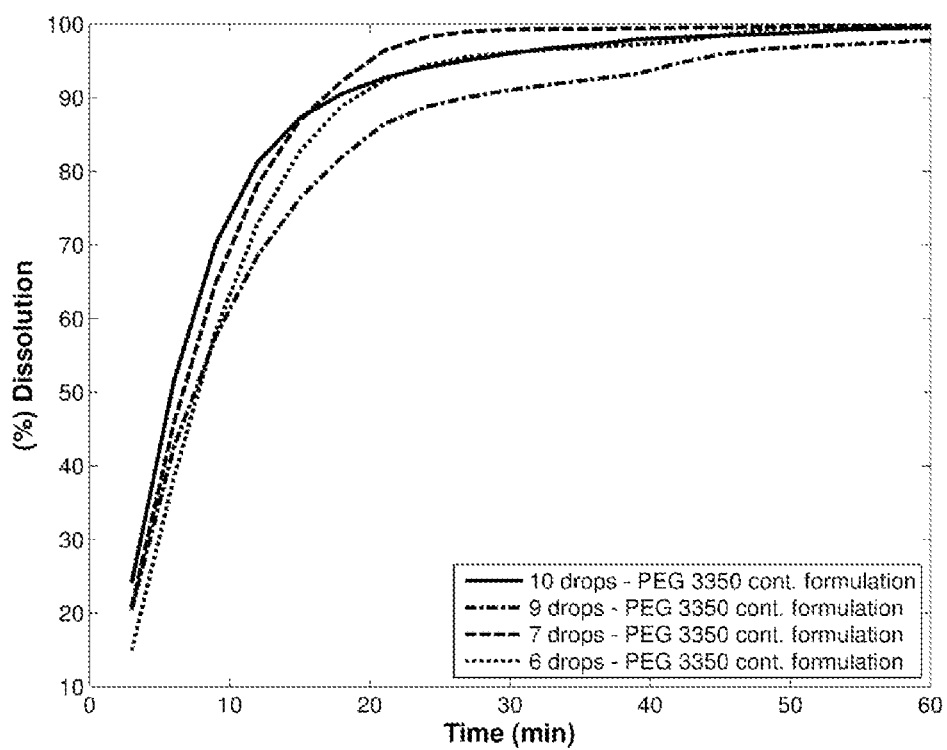
Figure 4 - Dissolution Profile of Naproxen – PEG3350 Drops (Example 6)

Figure 5 – XRPD Patterns of Naproxen, PEG3350, and Combinations (Example 7)
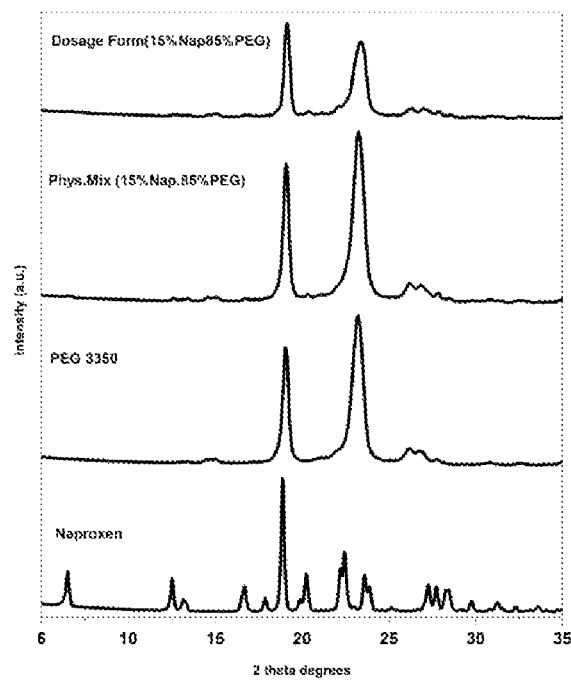

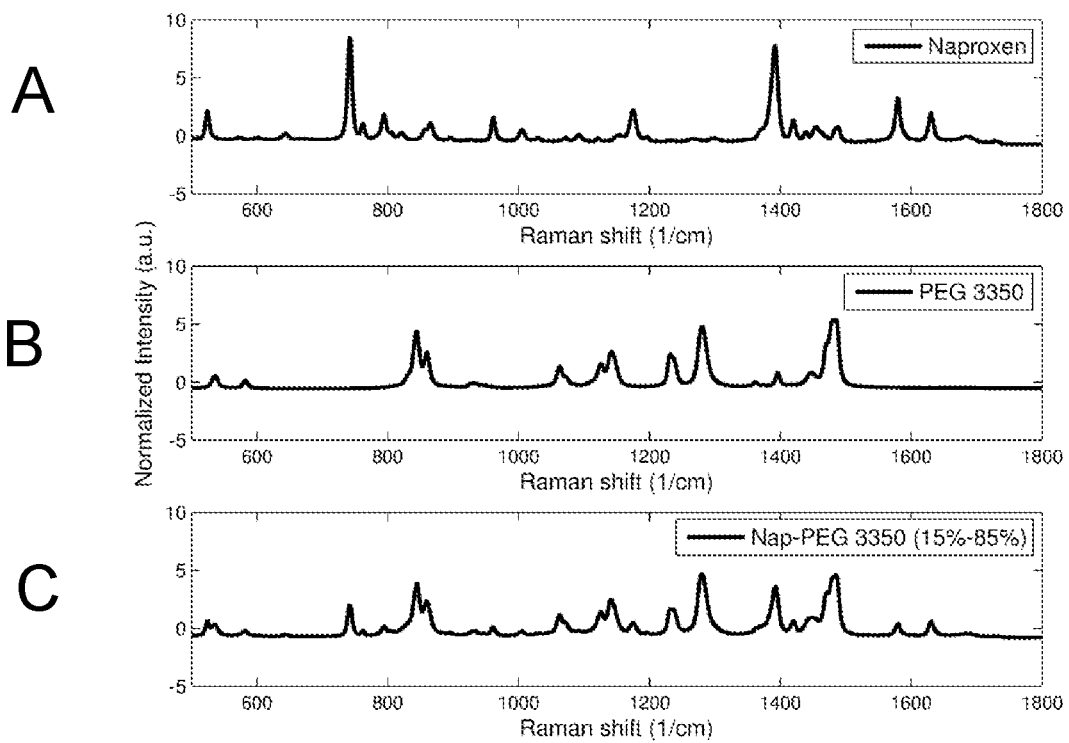
Figure 6 - Raman Spectra (Example 8)

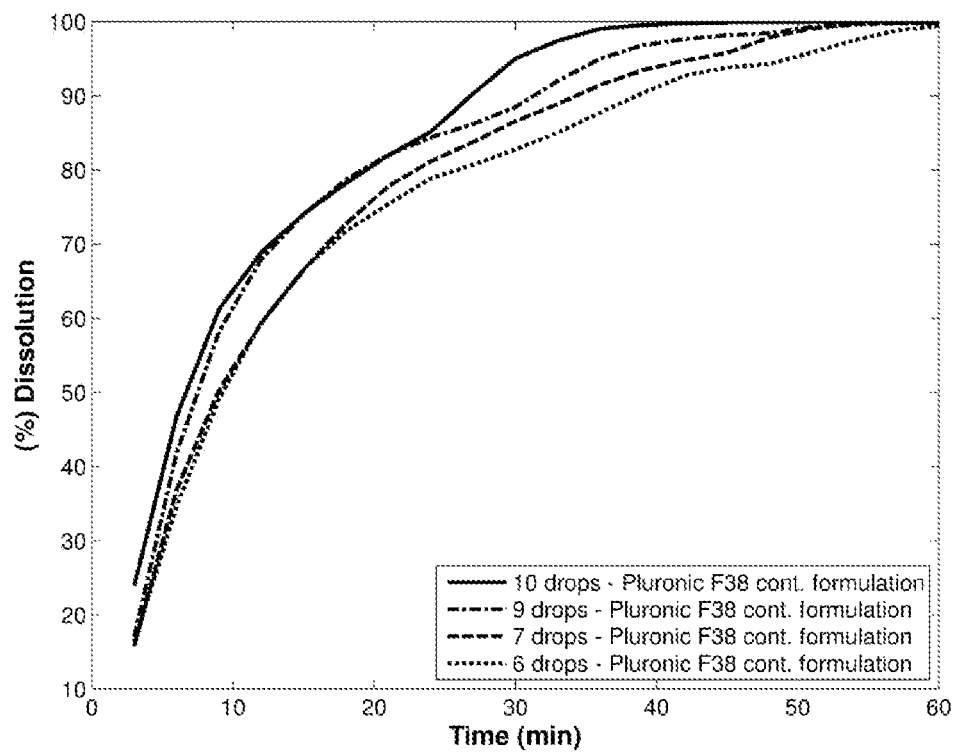
Figure 7 - Dissolution Profile (Example 17)

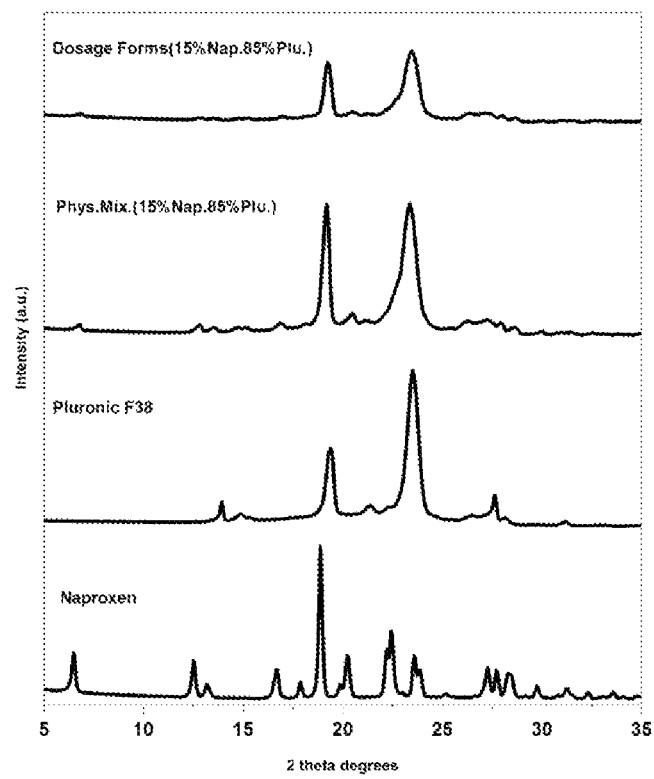
Figure 8 - XRPD Patterns (Example 18)

Figure 9 - Raman Spectra (Example 20)
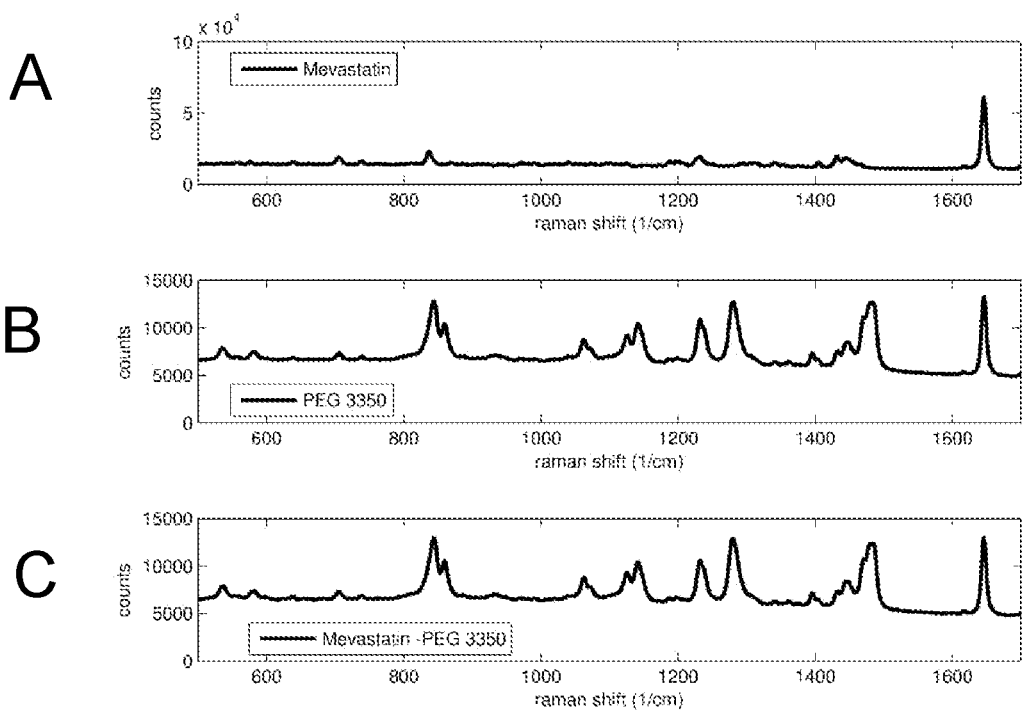

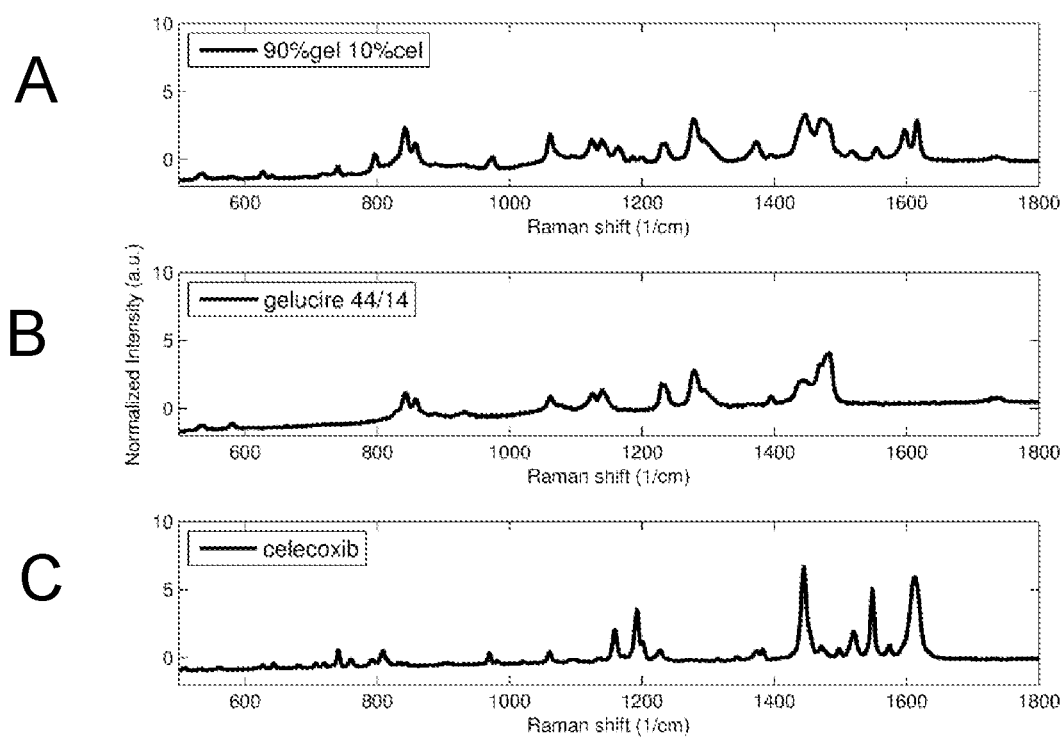
Figure 10 - Raman Spectra (Example 24)

Figure 11 – XRPD Patterns (Example 25)
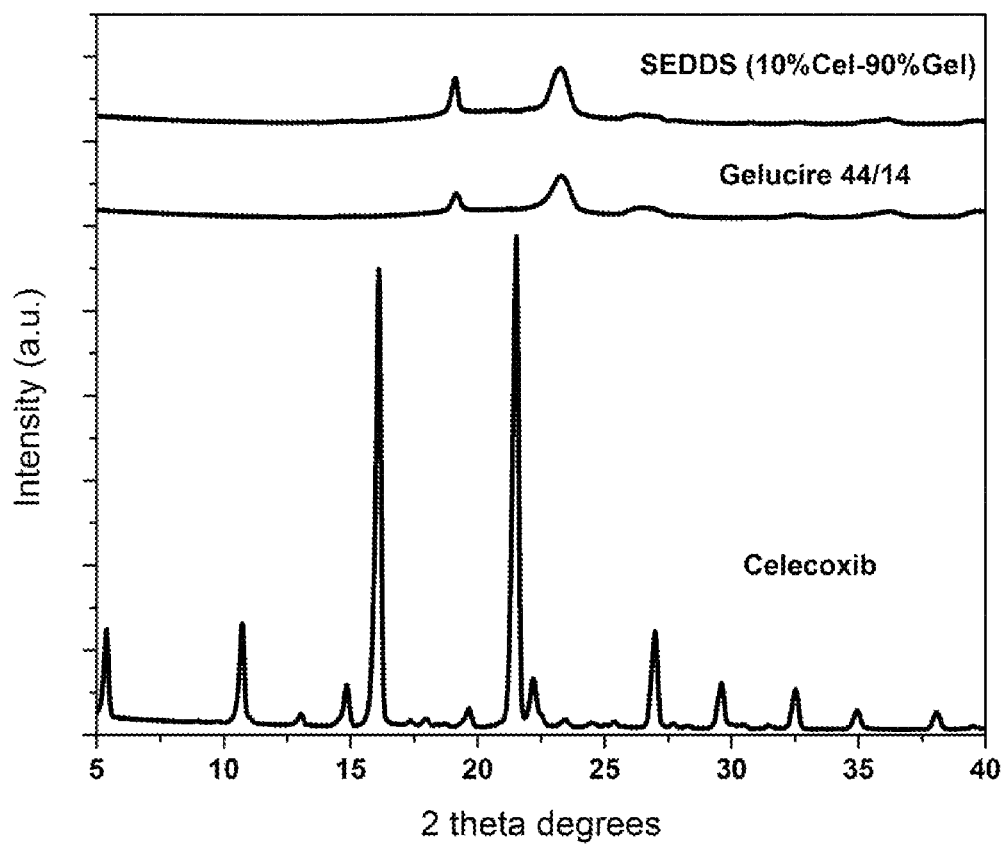

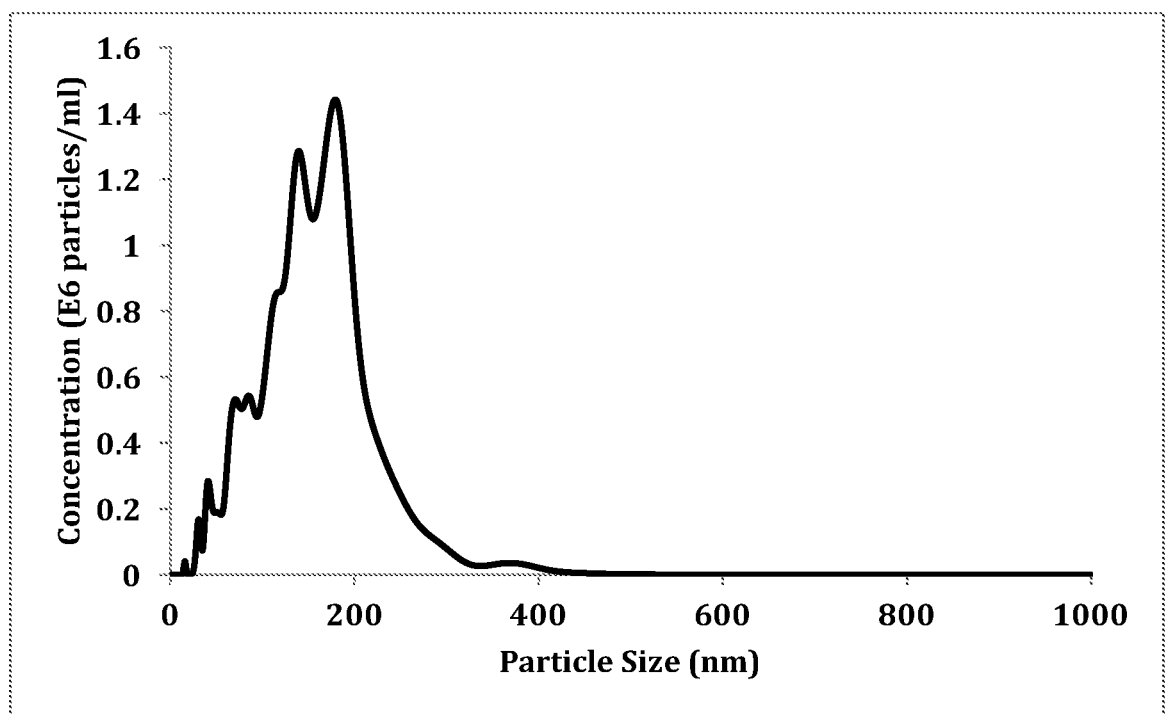
Figure 12 - Size Distribution Profile (Example 26)

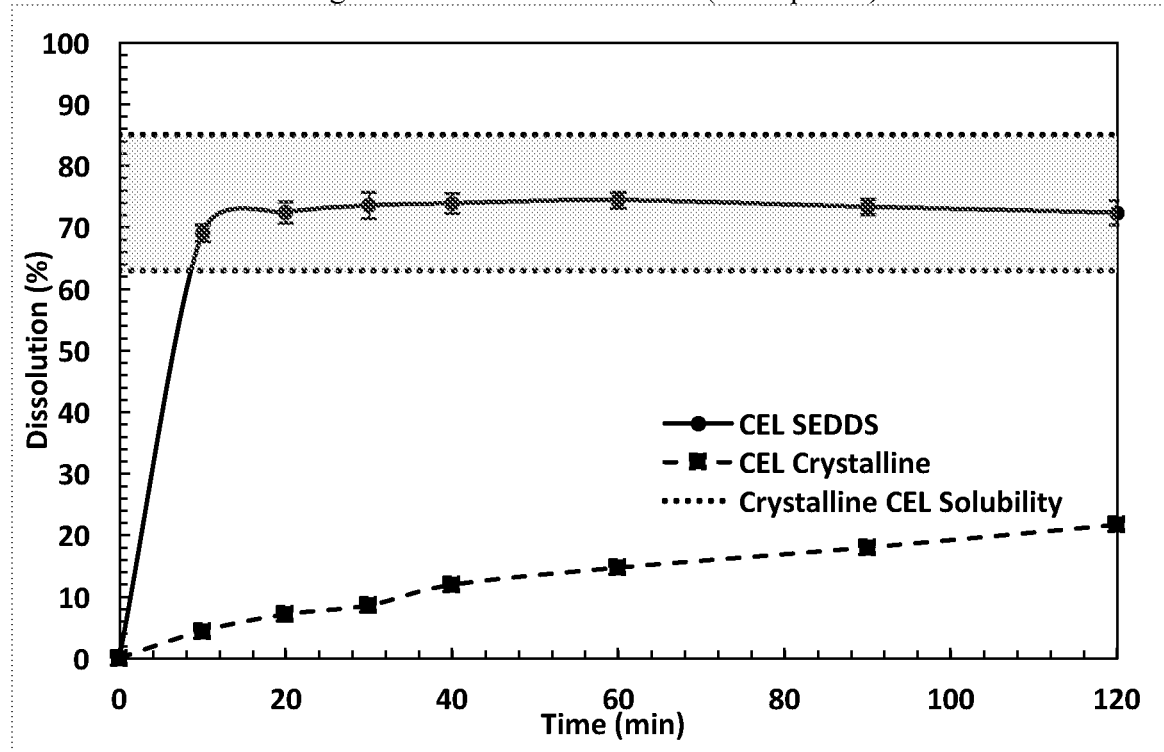
Figure 13 - Dissolution Profile (Example 27)

METHODS AND SYSTEMS FOR DEPOSITING ACTIVE INGREDIENTS ON SUBSTRATES

PRIORITY AND CROSS-REFERENCE TO RELATED APPLICATIONS

This application is related to, claims the priority benefit of, and is a U.S. national stage (under 35 U.S.C. 371) patent application of, PCT Patent Application Serial No. PCT/US2016/046217, filed Aug. 9, 2016, which is related to, and claims the priority benefit of, U.S. Provisional Patent Application Ser. No. 62/203,013, filed Aug. 10, 2015, The contents of each of the aforementioned patent applications are expressly incorporated herein directly and by reference.

STATEMENT REGARDING FEDERALLY SPONSORED RESEARCH OR DEVELOPMENT

This invention was made with government support under EEC-0540855 awarded by the National Science Foundation. The government has certain rights in the invention.

BACKGROUND

The batch processing mode that the pharmaceutical industry has traditionally used to manufacture pharmaceutical products provides significant challenges, including high production costs, long manufacturing times, scale-up difficulties, and recurring quality issues. The increasing competition and payer pressures are driving the pharmaceutical industry to deliver drug products in shorter time and lower cost. In recent years, the US Food and Drug Administration (FDA) introduced the quality by design approach and process analytical technology guidance to encourage innovation and efficiency in pharmaceutical development, manufacturing, and quality assurance.

With the implementation of FDA initiatives such as Process Analytical Technology and Quality by Design, the pharmaceutical industry is shifting focus to manufacturing processes that can be more closely managed in real time with more advanced process control. These innovative new processes are often small-scale continuous processes, as opposed to the traditional large-scale batch pharmaceutical manufacturing processes that featured very little in terms automation or control. Many advantages are gained by moving from batch operations to continuous operations: efficient processing rates, reduction in waste, improved product quality and increased process reliability.

In addition, the need for personalized medicine has grown in recent years. The justifications for personalizing dose amounts and product forms are numerous: certain drug substances exhibit innately high inter-patient variability, especially some oncology agents, and must be tuned to the patient if they are not to cause adverse effects; certain populations of patients such as pediatric and geriatric populations are underrepresented in standard drug studies, causing uncertainty when prescribing a suitable dosage amount for them; certain factors of patient medical history or genetic factors impose constraints on drug dosage amounts. Research has been done on calculating the best dosage amount of certain drugs for a given patient, based on medical, genetic and clinical factors. A hitherto missing component has been an effective way to make such doses.

Further, some otherwise efficacious drug formulations are not marketed by pharmaceutical manufacturers simply because their shelf life is short, less than 3 months for example. Due to supply chain lead times of many months, there is great reluctance for a pharmaceutical company to make drug products with shelf life shorter than 1 year. Therefore, a small-scale manufacturing technique also eliminates this problem, by manufacturing the exact amount needed when it is needed; therefore shelf-life constraints are made irrelevant, and it opens up many drug formulations that could not be pursued under traditional large-scale approaches. Small-scale processes therefore enable quick product changeover, flexible dosage forms, and personalized combination drug products. However, a suitable small-scale manufacturing technique has been missing from the field until now.

SUMMARY OF THE INVENTION

In one aspect of the invention, an active ingredient delivery system is provided comprising a fluid reservoir; a fluid-delivery apparatus in contact with the reservoir wherein the apparatus comprises a pump and a fluid-dispensing device; a real-time drop-imaging and measurement device; and a substrate holder comprising a stage and a substrate.

In a further aspect of the invention, a method for delivering an active ingredient to a substrate is provided comprising preparing a fluid comprising an excipient and an active ingredient; ejecting the fluid through a nozzle onto a substrate wherein the nozzle creates one or more drops of the fluid; and measuring the volume of the one or more drops.

In yet another aspect of the invention, a method for preparing a microdose of an active pharmaceutical ingredient is provided comprising the steps of preparing a fluid comprising an excipient and an active pharmaceutical ingredient; ejecting the fluid through a nozzle onto a substrate holder wherein the nozzle creates one or more drops of the fluid and wherein the substrate holder comprises a stage and a substrate; measuring the volume of the one or more drops; and processing the one or more drops to provide a microdose of the active pharmaceutical ingredient.

In still another aspect of the invention, a pharmaceutical microdose is provided prepared by the processes of the invention.

A further aspect of the invention provides a pharmaceutical microdose comprising (a) one or more active pharmaceutical ingredients and (b) one or more of a polymer, lipid, or surfactant, wherein the active ingredient is substantially amorphous, and the microdose is prepared from a single drop of a melt of the components in (a) and (b).

BRIEF DESCRIPTION OF THE DRAWINGS

FIG. 4 is a dissolution profile of the formulation set forth in Example 6.

FIG. 5 is a collection of x-ray powder diffraction patterns as set forth in Example 7.

FIG. 6A is a Raman spectra of naproxen as set forth in Example 8.

FIG. 6B is a Raman spectra of PEG 3350 as set forth in Example 8.

FIG. 6C is a Raman spectra of a 15% naproxen and 85% PEG 3350 melt formulation as set forth in Example 8.

FIG. 7 is a dissolution profile of the formulation set forth in Example 17.

FIG. 8 is a collection of x-ray powder diffraction patterns set forth in Example 18.

FIG. 9A is a Raman spectra of mevastatin as set forth in Example 20.

FIG. 9B is a Raman spectra of PEG 3350 as set forth in Example 20.

FIG. 9C is a Raman spectra of a 15% mevastatin and 85% PEG 3350 melt formulation as set forth in Example 20.

FIG. 10A is a Raman spectra of 90% gelucire 44/14 and 10% celecoxib melt formulation as set forth in Example 24.

FIG. 10B is a Raman spectra of gelucire 44/14 as set forth in Example 24.

FIG. 10C is a Raman spectra of celecoxib as set forth in Example 24.

FIG. 11 is a collection of x-ray diffraction patterns as set forth in Example 25.

FIG. 12 is a size distribution profile as set forth in Example 26.

FIG. 13 is a dissolution profile as set forth in Example 27.

DETAILED DESCRIPTION

Figure 1:
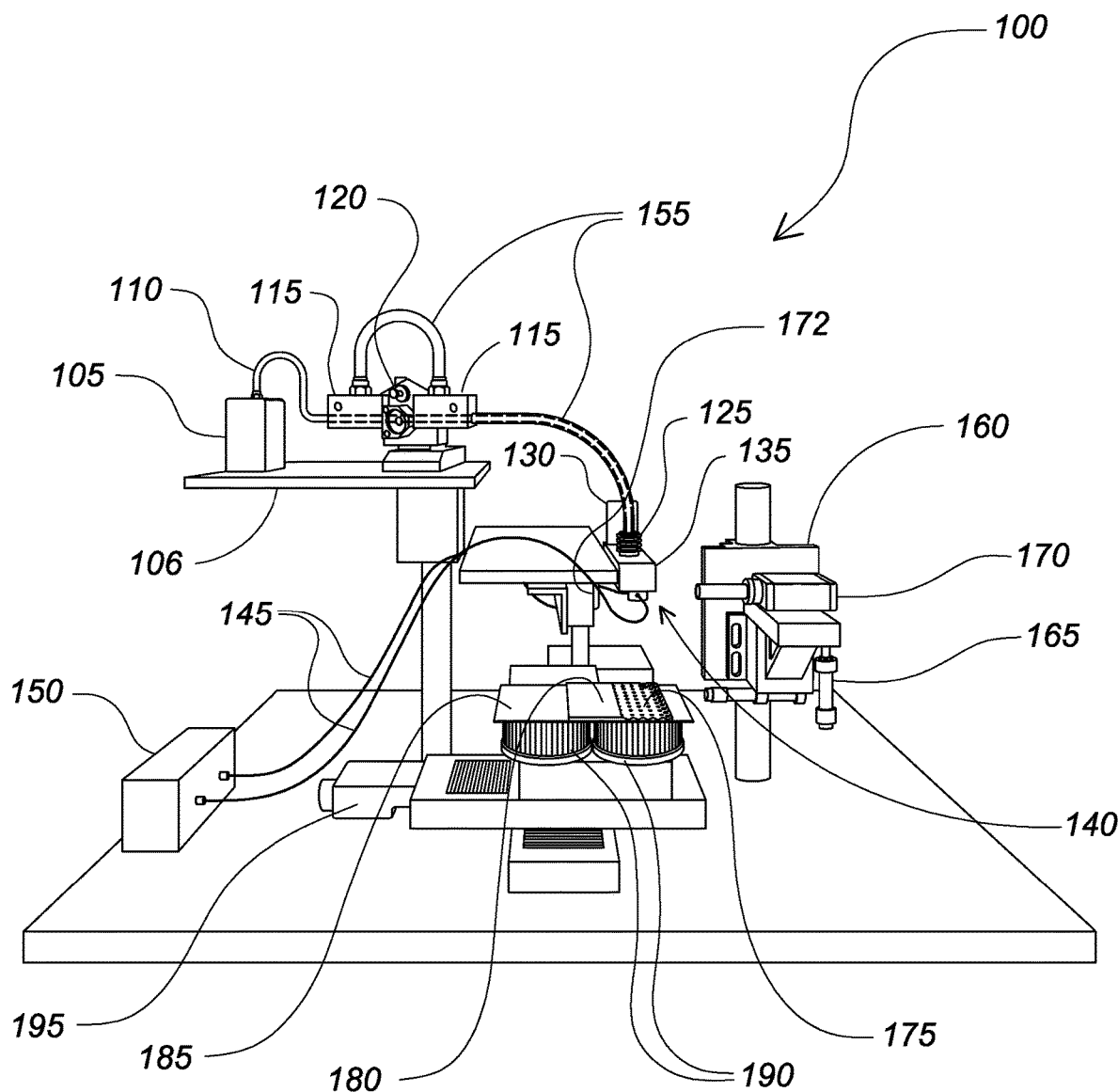
FIG. 1 is a perspective drawing illustrating an embodiment of an active ingredient delivery system of the invention.

The systems and methods of the invention include dropwise additive manufacturing systems and processes for solid oral drug production utilizing drop on demand printing technology for controllable deposition of active ingredients, such as active pharmaceutical ingredients ("API") onto edible substrates, such as dermal patches, sublingual or buccal products, injectables, syringes, tablets, film strips, vials, or capsules. Such systems and methods may be used to achieve individualized dosing for patients ("microdosing" and such a dose being a "microdose"). Through a combination of drop size and drop number, a dosage can be and reproducibly controlled to match the prescribed dose for a patient. In addition, the batch size can be as small as the number of tablets or drops required for one patient and the transitions from one dose to another made rapidly with minimal or no waste. Such a dropwise additive manufacturing system and methods may be used to advance personalized therapies by allowing the precise production of convenient solid oral dosages, for example, tailored to a patient on site at hospitals, clinics and compounding pharmacies. Further advantages include the added safety benefits in using small amounts of hazardous or potent APIs.

In various embodiments of the invention, the systems and methods herein apply closed-loop process management and control techniques, including on-line monitoring and fault diagnosis systems, which are easier and more effective to implement and control for small-scale fluid systems of the invention than for large-scale solid systems. Such techniques allow for error correction in, for example, drop shape and volume.

The systems and methods of the invention may be used to deliver active ingredients to substrates and print microdoses based on numerous different kinds of fluids comprising an active ingredient such as a pharmaceutically active ingredient. The systems and methods herein may be used to prepare fixed dose combinations of multiple APIs in the same dose or flexible dose combinations where different dosages of the APIs are deployed. Examples of fluids include including solutions, colloids, melts, suspensions, and emulsions. The fluids may also comprise an excipient. An example of an emulsion is a self-emulsifying drug delivery system.

In solutions, solid APIs are dissolved in a suitable solvent, wherein the solvent is considered an excipient. Other excipients, such as polymers, may be added if desired into the solution. The solution may be dispensed by the systems of the invention onto a substrate, where the solvent evaporates, leaving behind the solid API in a form to be used or as available for further processing such as coating. Temperature cycling may be employed at the substrate.

In melts, the excipient, or excipients, is usually one or more polymers. Other excipients may include lipids or surfactants. In such melts, solid APIs are mixed with such excipients and, optionally, one or more other non-polymer excipients. The resulting mixture may be heated in a reservoir until liquification or melting and then the liquid melt may be dispensed using processes of the invention onto a substrate. The substrate is typically temperature controlled so that that the melt may be cooled in a controlled manner on the substrate to solidification. Such cooling may be controlled so that cooling is not continuous. Temperature cycling may be employed, for example, to alternate between heating and cooling at the substrate. The cycling is often used to lower the temperature of the substrate over time, with intermittent periods of heating. Changes to temperature cooling rates may affect crystallization or solidification of APIs and thus may be advantageous. Examples of polymers used for melts include polyethylene glycols (PEGs), Pluronic® F38, and lauroyl polyoxyglycerides. Polymers with a melt temperature of less than about 100° C. and with low melt viscosity are typically used. Examples include polyethylene glycols (PEGs) with molecular weights of between 1,500-20,000 such as PEG3350.

For suspensions and emulsions, the API may be converted to a suspension or an emulsion as required by the use of readily available equipment (impinging jets or fluid jet mills, for example), and the formulation may then be dispensed by processes of the invention onto a substrate, where it retains or achieves its desired state and/or morphology until it is consumed. The temperature control of the substrate may likewise be used to influence state and or morphological properties and temperature cycling may be employed.

One advantage of the systems and processes of the invention is the rapid ability to manufacture formulations and change formulation ingredients and parameters to match desired microdosing outcomes in ways much faster than through traditional manufacture such as to identify suitable formulations for APIs with poor bioavailability. In traditional manufacturing contexts, preparing samples of each such formulation is time consuming and costly involving substantial operations to make an array of different formulations for testing whereas the systems and methods of the invention, can produce equivalent or greater variety of microdosing formulation testing in a small fraction of the time over traditional methods, which can then be delivered to patients on demand.

The properties of the API being deposited and the final form desired dictate which type of formulation should be used. Characteristics to consider include nucleation and crystal growth rates of the API during solvent evaporation at the substrate when using APIs dissolved in solvents or melt cooling at the substrate when APIs are dispersed on polymer melts, for example. Selection of the type of formulation, the type and amount of other formulation additives, and the conditions of the process such as the cooling rate profile, such as by using temperature cycling, at the substrate are based on the crystallization properties of the API and the desired phase outcome.

Numerous different classes and types of APIs may be selected including non-steroidal anti-inflammatories, painkillers, cytotoxic drugs, anti-depressants, among others. Drugs used in oral dosage forms may be included. Often, drugs are selected that have bioavailability challenges such as through poor dissolution, and are printed from melt or other formulations so as to provide for amorphous microdoses. Examples of such drugs may include BCS Class II and BCS Class IV compounds.

In other embodiments, other classes of pharmaceutically active ingredients may be used. The invention may be used with any active ingredient that can be prepared as a fluid as set forth herein wherein the fluid can be pumped through a nozzle to create drops for deposition onto a substrate.

By considering the crystallization behavior of the API and the formulation selected, the desired microdose can be prepared. For example, if a polymer is selected, a polymer may inhibit or promote crystallization. For inhibitory polymers, by increasing the ratio of polymer to drug, the proportion of the dosage form that is crystalline decreases. Therefore, printing a solution with a low ratio of polymer to drug may lead to a crystalline dosage form, with varying proportions of crystallinity that are dependent on drop size. Printing a solution with a high ratio of polymer to drug in such circumstances, however, may lead to completely amorphous forms, even for rapidly crystallizing drugs.

The substrate, usually temperature controlled, for receiving the API is typically a material that is edible and may be used as a finished dosage form for patient drug delivery. Examples of substrate dosage forms include dermal patches, sublingual or buccal products, injectables, syringes, tablets, film strips, vials, or capsules.

In these and other embodiments of the invention, a temperature-controlled reservoir is in contact with a fluid-delivery apparatus. The apparatus comprises a pump and a fluid dispensing device. The reservoir, which may be a cartridge, may be connected to the pump with an inlet tube. The reservoir is typically under temperature control so, for example, it may be heated to provide and maintain melts. Heating elements such as heating tape or heated air may provide thermal energy. The pump transports the fluid from the reservoir to the fluid dispensing devices through fluid transfer tubes where it is ejected onto a temperature-controlled substrate. The fluid transfer tubes, pump and fluid dispensing devices are under temperature control so, for example they can maintain melt temperatures. Typical heating elements are heating tape or heated air. The pump may be a positive displacement pump, a pump with flow control valves, a metering pump, a device that moves liquid with piezoelectricity, or a device that uses thermal effects to move liquid. Typically, the pump has a controller for adjusting pump parameters such as the velocity of the fluid being transported. Such capabilities are common, for example, on positive displacement pumps and positive displacement pumps are a preferred embodiment of pump. The pumps are also under temperature control so, for example, they can maintain melt temperatures. Typical heating elements are heating tape or heated air. The fluid dispensing device may be any device that dispenses fluid as drops onto a substrate such as a nozzle. The preferred embodiment of the fluid on exiting the nozzle is a drop or drops.

The parameters of the system and methods of the invention may be adjusted to change the dynamics associated with the drops which in turn affect the quality of the microdose formed on the substrate. Drop dynamics are affected by surface tension and viscosity. These two properties affect the ability of a nozzle to eject a drop. If the viscous forces and surface tension are too high, then drops may not eject. Typically, a viscosity of less than about 20 mPas is preferred. The surface tension of the material should be large enough so that the drops form into spheres and do not leak out of the nozzle while at rest.

There are three ways to produce drops from an orifice such as a nozzle: dripping, continuous flow, and drop-on-demand such as is used in the methods and systems of the invention. In the dripping method, drops emit from the nozzle as a result of only gravitational force. If sufficient pressure is applied to affect the drop flow, various controlled modes of drop formation can occur. In the continuous mode, a fluid is pumped through a nozzle to form a liquid jet and some form of periodic perturbation is applied to create uniform droplets. If the pressure is applied to the orifice in measured pulses using a transducer, one can obtain drops on demand. Thus, in the methods and systems of the invention, a fluid is held in a reservoir at a constant pressure and a pulse is applied to the transducer to create a drop as needed such as with a positive displacement pump. This pressure pulse causes a volume change in the fluid, which creates pressure waves and causes the drop to fall from the nozzle. In this way, a more precise and controllable drop is prepared as opposed to other methods. The user parameters that affect drop quality include nozzle diameter, temperature, and pump velocity. In many embodiments of the invention, a positive displacement pump is used to eject a fluid through a nozzle to create one or more drops. To increase reproducibility, it is desirable to have drops that are ejected from a nozzle have drop volumes typically be between about 1 µl and 50 µl per drop, including between about 1 µl and 35 µl per drop. Drop volumes further include between about 5 µl and 25 µl and also between about 10 µl and 15 µl all measured on a per drop basis. The mass of API, for example, in a drop may vary in some embodiments between 0 (if no API is used) up to 65 mg, including between 0.01 mg and 65 mg and between 10 mg and 65 mg. In other embodiments, a dosage of greater than 65 mg per drop may be used. The variability of drops is measured as the relative standard deviation ("RSD"), as that term is commonly understood. The relative standard deviation is often within 5%, including within 4%, 3%, 2%, 1%, 0.5%, 0.1%, 0.05%, 0.01%. In other embodiments it is between 1% and 3%. In still other embodiments it is between 0.008% and 0.9% including between 0.01% and 0.5% and between 0.03% and 0.1%, and between 0.03% and 0.9%.

Nozzle diameter may be measured with American Wire Gauge (AWG). Diameters of the invention range from 9 AWG to 29 AWG including from 13 to 21 AWG and including 15 or 17 AWG. Depending on the properties of the pump, nozzle diameters higher than 29 AWG or lower than 9 AWG are also embodiments herein. The nozzle is typically made of a non-sticking layer, such as Teflon®, or stainless steel.

Temperature control is a feature of the systems and methods of the invention. For example, when the fluid is a melt with a melt temperature greater than ambient temperature, then both the reservoir and the fluid-delivery apparatus are held at temperatures greater than ambient to prevent melt hardening in the system. The temperature of the fluid to be deposited may be controlled from the reservoir to the fluid dispensing device, such as a nozzle, to achieve desirable rheology, follow thermal stability constraints, maintain consistent material properties, and achieve predictable drop dynamics.

In many embodiments of the invention, a substrate holder is positioned so that it can receive drops from the fluid-dispensing device such as a nozzle. The substrate holder comprises a substrate and a stage. In many embodiments, the substrate holder further comprises a heater and a cooler. The heater may be a peltier device for example and the cooler may be electric fans, for example. A thermal plate may be mounted in between the peltier devices and the substrate so as to provide better temperature uniformity. There may be a further plate in between the thermal plate and the substrate for sample holding purposes, for example.

Controlling the substrate conditions after deposition may be used to affect an active ingredient's, such as a pharmaceutically active ingredient's, crystallization behavior. As in traditional crystallization processes, temperature directly influences both the nucleation rate and the crystal growth rate.

When printing solvent-based formulations, the cooling or heating rate of the substrate after deposition also affects the evaporation of the solvent. The evaporation of the solvent then affects the fluid composition and thus the nucleation and crystallization rates as well. Therefore, the crystallization behavior of the active ingredient depends on the solvent formulation properties, more specifically, concentration, temperature, and the solubility properties of the active ingredient in the solvent. The temperature profile of the substrate should be optimized to balance the cooling or heating of the substrate to affect solvent rate and thus production time and also heating the substrate to control the drug morphology.

For example, a fast-evaporating drop may yield an amorphous active ingredient whereas a slower-evaporating drop due to a cooler substrate may yield a crystalline active ingredient. Amorphous materials are generally more soluble than crystalline materials and solubility and dissolution rate are often critical parameters in drug delivery. Temperature control may be achieved by having the substrate in thermal contact directly or indirectly with a peltier device under computer control, for example in connection with a cooler. Having both a peltier device and cooler allows for temperature cycling. Similar temperature control factors are important in melts, for example, where the active may solidify in a disordered state, such as an amorphous form, a crystalline state, or partially crystalline state. The nature of the state may affect dissolution and thus bioavailability.

In these and other embodiments of the invention, a real-time drop-imaging and measurement device may be used to record both an image of the drop as well as various parameters associated with the shape, size and dynamics of the drop.

When fluids emerge, such as by ejection as a drop or drops, from the fluid-dispensing device, such as a nozzle, they may be imaged. Feedback control may be applied to the production of subsequent drops and monitoring of drops may be done by real-time imaging. Imaging each drop that is formed may be done by conventional means and may allow for the monitoring of several aspects of the process. Drop volume, and thus amount of drug per drop, may be calculated as well as calculating the center of the drop and drop trajectory. Conventional software may be implemented for calculating such parameters such as LabVIEW®. The information can then be used in a form of feedback control to adjust future drops to return the process to within desired operating bounds.

In typical operations, a photosensor and fiber optic cables may be used to trigger the camera, so the camera captures an image at the same point in the trajectory for each drop. The camera is backlit, typically with an LED light, to improve image quality. This allows for a consistent view of the drop and also for comparison between sequential drop images. The triggering of the camera via the photosensors also allows for the camera code to be incorporated into the overall LabVIEW® code, but to still run independently of the drop deposition and control codes.

After LabVIEW® acquires an image, for example, it displays the image on the program interface. By calculating each drop volume and knowing the concentration of the printing solution, the amount of API in each drop may be calculated. The volume may be estimated by any number of methods known in the art.

The stage of the substrate holder may be used to position the substrate for receiving drops. Drop positioning is accomplished by locating the printer nozzle above the desired location on the substrate before ejection. The x-y-staging and synchronization logic allow for precise drop positioning on the substrate while printing and enables layering of different drugs for either a fixed combination dose or flexible combination dose. The drops may be deposited in a grid structure. The behavior of a drop on impacting a solid surface is controlled by a number of physical processes including the drop velocity, size, drop material properties, distance from the surface, and surface properties. Upon impinging the drop can splash, spread, or even rebound. In order to achieve a single isolated drop without splashing or spreading, the physical process parameters may be suitably selected.

In one embodiment of the invention, a microdose is created by depositing a single drop onto a substrate, such as when the system is used to deposit single drops onto a tablet or film. The creation of a pattern of multiple drops utilizes a staging mechanism to move the substrate in relation to the nozzle, by either moving the nozzle over the substrate, as is performed in most inkjet printers, or by moving the substrate underneath the nozzle, or both. The staging mechanism is synchronized to print a desired drop pattern onto the substrate such as in a grid-like pattern allowing for efficient use of the substrate with enough space between each drop to avoid interactions.

Another consideration of the drop deposition pattern is whether the drops will be deposited in a single layer or in multiple layers. Drops can be layered to achieve a desired drug loading that is not obtained with one layer of drops, or the dosage form could include layers of drops of multiple APIs to create a combination product. In either case, the drop will not simply spread over the substrate as it would if it were a single layered drop; rather, the drop will interact with both the substrate and the previously deposited drop and may be absorbed by the substrate. In another embodiment, an intermediate layer between each drop containing only polymer and no API could be deposited. Thus, preparing a microdose, one or more drops may be used when depositing onto a substrate. For example, in some embodiments, a single drop is used to deposit onto a substrate. In other embodiments two drops are used. In still other embodiments three drops are used. Other embodiments include any one of 4, 5, 6, 7, 8, 9, 10, 11, 12, 13, 14, 15, 16, 17, 18, 19, or 20 drops. Still other embodiments use greater than 20 drops per microdose.

Several different online and off-line methods can be used for verifying drug solid-state form or product quality after creation of the microdose. For example, X-ray powder diffraction (XRPD) can be used to verify the crystal structure and quantify what portion of the drug is crystalline. Raman or near-infrared (NIR) spectroscopy can be used to analyze the different spectral patterns associated with different polymorphic forms. Raman and NIR spectroscopy are particularly applicable to these types of dosage forms as they are noninvasive and are suitable for online use. They can also be used to analyze other aspects of the dosage form, such as feature size and shape distribution. Other analytical techniques include Raman imaging, Raman microscopy, NIR imaging, gravimetry, chromatography such as HPLC, differential scanning calorimetry, thermal gravimetric analysis, gas pycnometry, particle size analysis, tapped density measurements, and dissolution techniques.

After creating and analyzing the dosage form, various other steps can occur in terms of postprocessing. The deposited drug form could be coated, as is carried out often with tablets, to make the dosage more palatable to patients, or to influence the rate of dissolution in the gastrointestinal tract. The dosage form could also be prepared to receive another layer of API to create a multilayered combination drug such as with a fixed dose combination or a flexible dose combination.

In these and additional embodiments of the invention, pharmaceutical microdoses prepared by the methods of the invention are provided. Such pharmaceutical microdoses may be directed to preparing a melt of an API in a polymer such as a PEG and pumping that melt with a positive displacement pump to a nozzle, all at temperatures greater than the solidification point of the melt. The nozzle diameter and fluid velocity from the positive displacement pump may be adjusted so that suitable drops are formed ejecting from the nozzle. The drops may be ejected onto an edible substrate which is then cooled to solidify the melt to form microdoses. Single or multiple drops may be used to create each microdose and the substrate may be advanced automatically to create additional doses. Multiple layers may be made with API on each layer, or layers without API, or with multiple APIs. The resulting microdoses may then be coated if desired. Various analytical techniques may be used to evaluate microdose quality.

In other embodiments of the invention, microdoses are provided comprising one or more active ingredients and one or more of a polymer, lipid or surfactant wherein the microdose was prepared from one or more drops of a melt comprising the components. Such microdoses may further include one or more excipients which were present in the melt. Such microdoses may further be coated and may be substantially amorphous or partially crystalline.

FIG. 1 shows a perspective view of a system of one embodiment of the invention 100. Reservoir 105 on mount 106 is connected via fluid transfer tubing 110 to positive displacement pump 120 and nozzle base 125. Heated air tube 155 connects the nozzle base 125 through housing units 115 where it exhausts. The fluid transfer tube 110 is located inside heated air tube 155 in between the nozzle and the housing unit 115 which is located furthest from reservoir 105. Nozzle base 125 is attached to nozzle holder 135 and heater 130 supplies the heated air to nozzle base 125 and hot air tube 155.

Two aluminum plates 140 are positioned transverse the lower side of nozzle holder 135 and perpendicular to the plane of FIG. 1 and configured to each receive one fiber optic cable 145 in apertures in each plate 140 such that an open end of each fiber optic cable is positioned in each aperture and the fiber optic cables are aligned such that when a light beam passes between them, that beam is parallel to the plane of the lower surface of nozzle holder 135. Photosensor 150 is connected to the two fiber optic cables 145 such that one fiber optic cable is a light source and the other is a light detector.

LED light 172 is mounted to the same assembly holding the nozzle holder. Camera 170 is mounted on mount 160 and the z-axis position is controlled by controller 165. Camera 170 is configured so that when drops are ejected from the nozzle in nozzle base 125, the drops are in the field of view of the camera. LED light 172 is mounted so that it provides light for the field of view in the same line as the camera and the drop.

Substrate 175 sits on holder 180 which is in contact with thermal plate 185. Peltier devices (not shown) sit underneath 185 and fan coolers 190 are positioned between the thermal plate 185 and x-y moveable stage 195.

Figure 3:
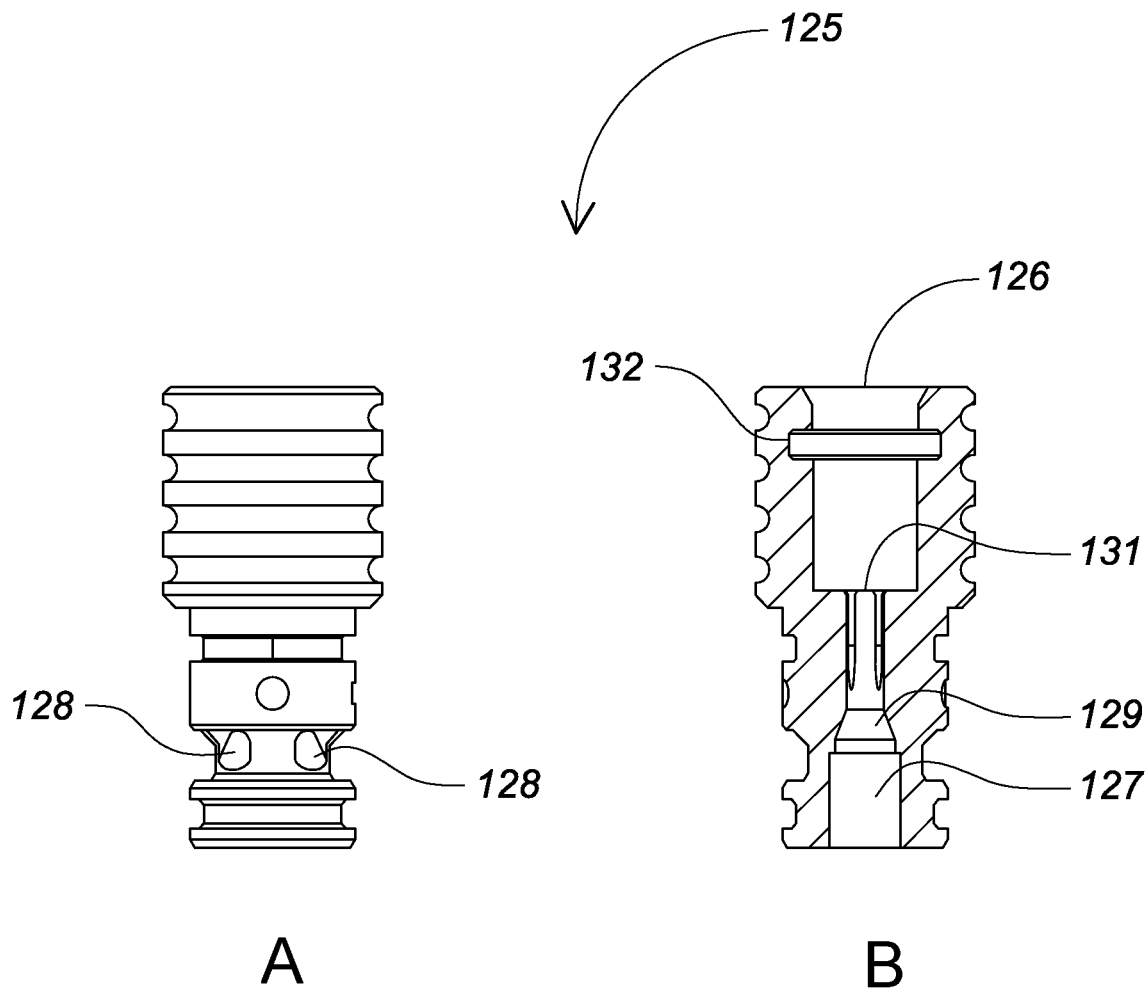
FIG. 3A is a perspective drawings of a component in FIG. 1.
FIG. 3B is a sectioned drawings of a component in FIG. 1.

In one embodiment, a fluid comprising an excipient and an active ingredient may be introduced into reservoir 105 where it is pumped by positive displacement pump 120 through fluid transfer tube 110 through both the nozzle base 125 and the nozzle sitting inside the nozzle connector as seen in FIG. 3A and FIG. 3B. The fluid is ejected from the nozzles as one or more drops and, when positioned in the drop trajectory path, substrate 175 receives the one or more drops. Camera 170 images the drops after ejection and the data is transmitted to a computer where the volume is calculated. The substrate is heated by the peltier devices underneath thermal plate 185. By controlling the cooling and heating rates of the substrate, such as by temperature cycling, one can control the solidification parameters, such as the degree of crystallization, of the active ingredient in the fluid on the substrate. In many embodiments, the rate of cooling at the substrate is not monotonic, such as by temperature cycling, and further may be under computer control. The cooling may go below ambient temperature.

Figure 2:
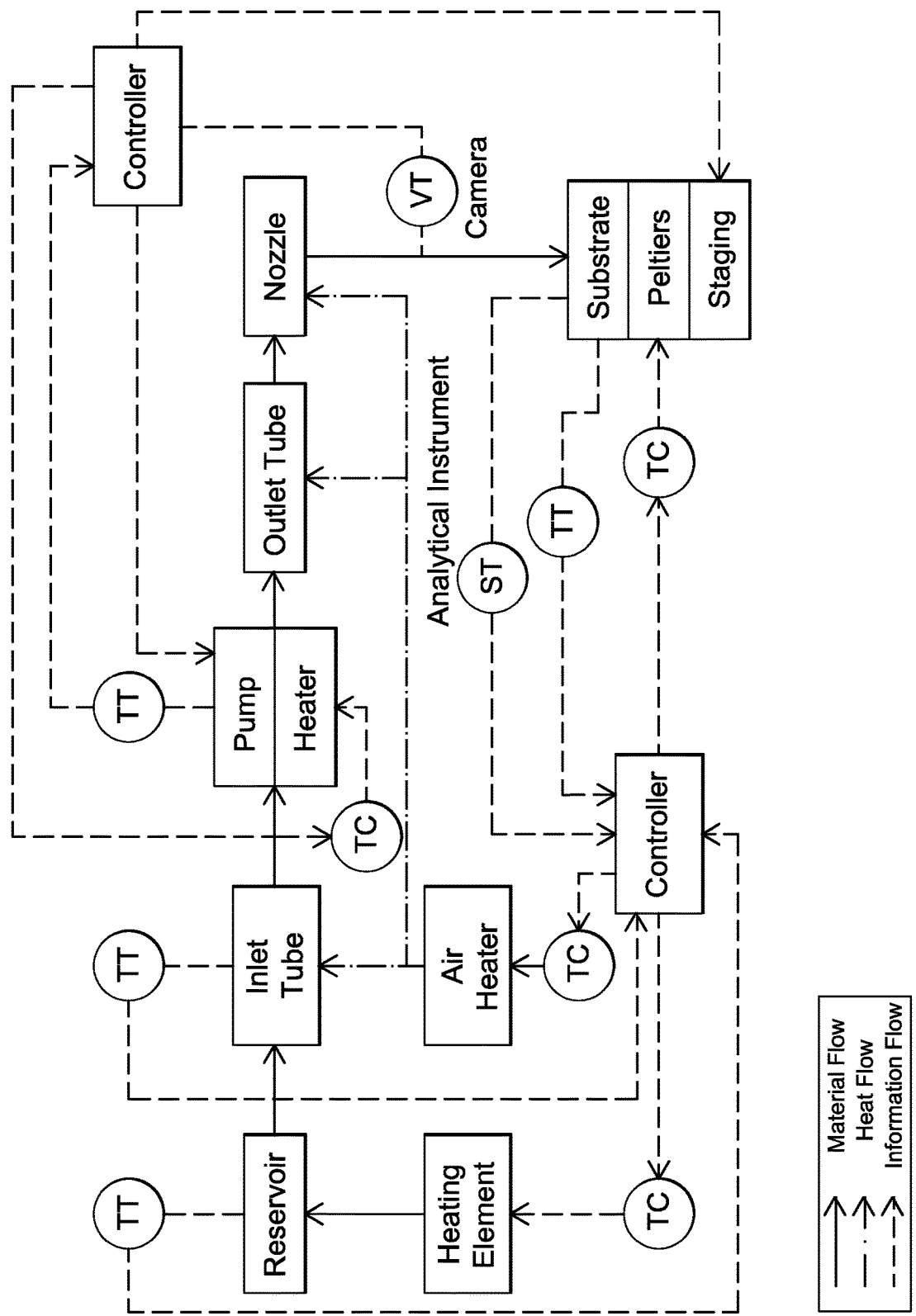
FIG. 2 is a block diagram illustrating an embodiment of an active ingredient delivery system of the invention.

FIG. 2 is a process diagram of one embodiment of the system and methods of the invention. In this embodiment, a reservoir, such as a cartridge, contains a fluid comprising an active ingredient and an excipient. The fluid is pumped by a pump, such as a positive displacement pump, through an inlet tube and an outlet tube, via the pump, for ejection as one or more drops at the nozzle.

The reservoir may be heated with a heating element, such as heating tape or hot air. A temperature transducer converts the temperature data to a signal for a controller, such as a computer or a user, and a temperature controller controls the energy supplied by the heating element. Likewise, an air heater heats the inlet tube, the outlet tube, and the nozzle with temperature data flowing to a controller. The pump here is under separate heater control as indicated.

The substrate is heated by peltier devices and may be moved by a stage. The substrate may also be cooled, although coolers are not indicated here specifically. The peltier devices are under temperature control and an analytical instrument may be used to collect data wherein a signal transducer (ST) converts the data into a signal for the controller. A video camera captures video information which is converted into a signal (VT) for image analysis and volume measurement.

FIGS. 3A and 3B show a perspective and sectioned view of nozzle base 125, respectively. Opening 126 is for receiving hot air tube 155. The nozzle fits into opening 127 and can be screwed into place. Air holes 128 are positioned around the circumference of the nozzle base and allow for heated air from heater 130 to go through tube 155. A space for a ferrule is at 129 where fluid transfer tube 110 is secured at the top of the nozzle when it is in place. Aperture 131 indicates where the fluid transfer tube, which sits inside heated air tube 155, sits in nozzle base 125. O-ring 132 is positioned to help secure hot air tube 155 when present.

EXAMPLES

System Components and Process Parameters—Example A

In many embodiments, a system for delivering active ingredients using the following components is provided. Examples of operational processes that may be used according to certain embodiments of the invention is also provided in this example.

Pump: IVEK Digispense 10 single-channel positive displacement pump, with controllable drop volume, number of drops per operation, and controllable drop pinch-off.

Reservoir: Glass vial, 15 ml, reusable or disposable, sealed or unsealed.

Tubing: Teflon® and/or polyethylene tubing in a size suitable to the rheology of the drug formulation, typically ranging from $\frac{1}{16}$" outer diameter to $\frac{1}{8}$" outer diameter, with associated ferrules, O-rings and fittings.

Nozzle: Teflon and/or stainless steel nozzles with different diameters suited to the rheology of the liquid and to the desired drop pinch-off characteristics.

Vision system: A Manta G-146B camera connected to a Banner D10 photoelectric sensor and a Spectrum Illumination XS40-WHI backlight.

Staging system: A Newport XY stage moves the substrate in two dimensions under a fixed nozzle in this specific realization. The stage is controlled by a motion controller, and can achieve the deposition of API onto the substrate in any desired pattern, including regular grids.

Temperature control: reservoirs are heated with Omega nichrome heating elements and an Omega temperature controller. The pump is heated with cartridge heaters controlled by an IVEK temperature controller. The tubing is heated by hot air in a double-pipe layout, which is controlled by an Omega inline air heater and an Omega controller. If desired, the double-pipe layout can be replaced by electrically heated tubing with integrated heating elements. Substrates are heated or cooled as required by thermoelectric devices controlled by a TETech controller.

Automation: Automation and process management functionalities have been implemented in LabVIEW®. The user enters certain inputs (how many drops to dispense in what pattern, what temperature to use for each unit, and where the recorded data should be saved). The program then executes, depositing the drops in the specified pattern. For each drop, an image is taken by the camera and analyzed by the LabVIEW® program to calculate its volume and to detect any incipient abnormal behavior indicative of a process fault. If the situation is normal, the image and the calculated drop volume are recorded, otherwise the operator is informed of the specific nature of the abnormal behavior; the program takes corrective action automatically if it is able to, otherwise it halts execution until the problem is corrected. In addition to the drop image and calculated volume, it also saves multiple parameters for each drop, such as temperatures (both actual and targeted), heater currents, pump settings, and morphology data. It also stores information needed to track individual drops within a larger substrate (for example, row and column indexes in a grid). Dose frequency ranges from between about 2.5 seconds per dose to 0.1 seconds per dose. Frequency may be less than 0.1 seconds per dose in some embodiments.

System Components and Process Parameters—Example B

In many embodiments, a system for delivering active ingredients using the following components is provided. Examples of operational processes that may be used according to certain embodiments of the invention is also provided in this example.

The drug material is stored in the reservoir and then pumped through an IVEK Digispense 10 single-channel positive displacement pump. The pump is connected to a custom controller that allows for variation in volume strokes and RPM. This controller allows for automatic operation via LabVIEW® or manual operation. The size of each drop can be adjusted by using a thumb screw on the pump to change the displacement of the piston within the cylinder in pump. The tubing connected to the inlet and outlet of the pump is Teflon tubing with $\frac{1}{8}$" O.D. and $\frac{1}{16}$" I.D. with corresponding Teflon ferrules and fittings. After passing through the pump and the tubing, the drug material ejects through a nozzle. Teflon or stainless steel nozzles with different diameters (13, 14, 15, 17, 19, or 20 AWG) can be attached to the nozzle holder. The ejected drops are monitored using a Manta G-146B camera-based imaging system with a Banner D10 photoelectric sensor and an XS40-WHI backlight from Spectrum Illumination. The nozzle is positioned over the substrate, which is located on a Newport xy stage that is controlled by a motion controller. The use of the xy staging allows for printing of the material in any desired pattern, including a regular grid. The system is attached to a Newport breadboard with various Newport mounting accessories and plates.

A LabVIEW® program allows for synchronous execution of the pump, staging, and camera and also incorporates the control and monitoring methods discussed previously. The user enters various inputs into the program including drop settings such as grid pattern of the drops and distance between the drops. Other inputs include temperature control of the reservoir, fluid transfer device, and substrate. Various process parameters such as temperature, time, location of drop, a drop image and image analysis, are saved for each drop.

Image Analysis and Calculations—Example C

In many embodiments of the invention, after an image is acquired in the LabVIEW® program, the program converts the image to an array in order to analyze the contrast of the image on a pixel-by-pixel basis. Since the image is in grayscale, each pixel is assigned a value 0-255 that represents the darkness of the pixel. The use of the high intensity backlight creates a high contrast between the drop and the image background, so the drop is mostly dark (low pixel values) and the background is mostly light (high pixel values). If the pixel value is less than a threshold brightness value (for example 80), this denotes a dark pixel that is part of the droplet. An array of Boolean values is created by converting all pixel values less than the threshold to "1" and all other values to "0."

The program then analyzes each row of pixels to find the diameter of the drop. It finds the index of the first and last instances of a "1" to detect the drop edges. Subtracting these two values gives the diameter of the drop at that row. It is necessary to calculate the diameter this way, rather than just summing the "1" values in the image array, to account for the bright white spot in the center of the image that refracts the backlight. This method essentially "fills in" that spot in the image and then includes it as part of the drop volume.

After finding the diameter of one specific row, the program calculates the cross-sectional area at that row, assuming that the drop is symmetric around the axis and thus the area around the axis is a circle. It then calculates the volume of this slice of the drop in assuming that it is a cylinder with a height of one pixel. It repeats this for each row of the image before summing all of the cylinders' volumes and calculating the volume of the entire drop in voxels. The volume in voxels is then converted into microliters using the pixel width and pixel height of the camera's sensor (4.65 µm for the Manta G-146B).

The volume calculated for each drop is recorded and also displayed to the user. Besides being able to use the volume calculations to analyze the consistency of drops throughout the process, it is also possible to keep a running total of the total volume deposited. For melt-based formulations, this is equivalent to knowing the total amount of solids deposited on the dosage form, and thus, with the known concentration, it is possible to keep a running total of the amount of drug on the form. However, for solvent-based formulations, it is also necessary to know the density of the printing material in order to deduce the mass of each drop and thus the mass of the solids within the drop.

Example 1—Materials and Formulation—Naproxen I

In this example, naproxen is chosen as the model API to form melt formulations either with the polymer polyethylene glycol with a molecular weight of 3350. Naproxen (NAP) was purchased from Attix Pharmaceuticals (Montreal, QC, Canada). PEG 3350 was provided by The Dow Chemical Co. (Midland, Mich.). Naproxen and the polymer PEG 3350 were mixed in (15:85) weight ratio. The mixture is comelted at 65° C. until completely melted. The melt formulation is printed on polymeric films prepared with hydroxypropyl methylcellulose (HPMC) (E50) and PEG 400. HPMC (E50) is purchased from Sigma Aldrich Corporation (St. Louis, Mo.). PEG 400 likewise was provided by The Dow Chemical Co. (Midland, Mich.).

Example 2—Film Preparation

In order to make a 5% (w/v) polymer solution, 0.6 gr HPMC powder (E50) and 0.4 gr PEG 400 were dissolved in 20 ml water at 90° C. The 5% (w/v) HPMC-PEG 400 solution was stirred at room temperature overnight to ensure that the polymeric chains were homogeneously dispersed in the solution and cast onto a Petri glass. After drying was completed, the film was peeled off.

Example 3—Methodology

After deposition of the drops onto the film, the resulting dosage forms were analyzed to determine whether the different formulations would affect the dissolution behavior of the API. The dosage forms were created and analyzed at the same time and thus varying ambient conditions, such as relative humidity, were not impactful on the results.

Example 4—HPLC

In order to check the chemical stability of naproxen under production, HPLC experiments were performed on the dosage forms, which were intentionally subjected to 70° C. for 15 min during production. The HPLC experiments showed that naproxen found in the dosage forms is stable. The amount recovered is the same of the amount present in the dosage forms and no degradation peaks were observed.

Quantification of the drug in the dosage forms was done using an Agilent 1260 infinity high performance liquid chromatography (HPLC) system using an Agilent plus C18 5 µm, 2.1×150 mm column (Agilent Technologies, CA). The mobile phase consisted of acetonitrile (ACN) as the organic phase and pH 2.5 phosphate buffer as the aqueous phase. Isocratic elution was performed on the samples at a flow rate of 0.5 mL/min with the mobile phase consisting of 60% aqueous phase and 40% ACN. Naproxen was detected at a wavelength of 210 nm using an ultraviolet detector. The retention time of naproxen was 4.5 min using the method listed above. A calibration curve was plotted from 1 g/mL to 100 g/mL with a R2 value of 0.9999. For analysis of the dosage forms, individual drops of naproxen-PEG 3350 were dissolved in ACN and diluted appropriately to obtain the concentration in the range of the calibration curve.

Example 5—Reproducibility of Dosage Amounts

Different drop sizes are used to produce the dosage forms with target dosage of 15 mg of API. The different drop sizes are obtained by changing the pump and printing operating parameters such as nozzle diameter, displacement, volume strokes and rate. The number of drops needed to reach the target amount varied for each printing setting and was determined experimentally before producing the dosage forms. To analyze reproducibility, HPMC-PEG 400 film measuring 2 cm by 2 cm was weighed on an Omega AL-201s balance. Next, a specific number of drops were deposited on the film to reach the target dosage amount. The films were then subjected to room temperature until the deposits solidify. After solidification of the drops, the films were weighed again to determine the total mass of the deposits on the film. The amount of drug was determined by multiplying this mass of solids by the composition of drug in the solution (15%). These results were then used to analyze how consistently and accurately the dosage forms are created.

To demonstrate different drop sizes, two intermediate sizes of nozzles (i.e. with internal diameters of 15 AWG and 17 AWG) are used. The pump settings are determined to achieve consistent drop formation for both formulations using these nozzle sizes. Using the DAMPP system, dosage forms are produced by printing different sizes of drops on HPMC-PEG films as the substrate. The reproducibility of the dosage forms so produced is shown in Table 1. The relative standard deviation (RSD) is less than 2%. These RSD values are well within the 5% RSD limit required by the FDA.

TABLE 1

| Formulation | Number of drops printed | Average dosage amount (mg) | RSD (%) |
| --- | --- | --- | --- |
| 15% Naproxen | 10 | 14.32 | 0.56% |
| 85% PEG 3350 | 9 | 15.69 | 0.18% |
|  | 7 | 16.13 | 0.05% |
|  | 6 | 15.53 | 1.30% |

Example 6—Dissolution Testing

The dissolution test was conducted using USP-I apparatus (Varian VK 7010) at 100 rpm. The dissolution media consisted of the USP phosphate buffer solution of pH 7.4, which was maintained at 37° C. The experiments were performed in sink conditions to prevent the drug from saturating the dissolution media. The experiments were run for 90 minutes, and aliquots of the dissolution medium were collected at intervals of 3 minutes through 35 micron full flow filters (Agilent filters) by a peristaltic pump. Sample absorbance was measured by a UV spectrophotometer (Cary 50) at 243 nm. Absorbance values from the spectrophotometer were used to calculate the percent release of the API from the films. Each experiment was performed in three replicates.

Dissolution testing was performed on the dosage forms produced with different sizes of drops and different formulations. In FIG. 4, the dissolution profiles of the dosage forms with the formulation containing 15% naproxen and 85% PEG 3350 are shown. Dissolution of 98% was achieved in one hour and 85% within 20 minutes. There are slight differences in the dissolution profiles of the dosage forms printed using different drop sizes. This is due to the effect of the cooling temperature gradient within the drops as they are solidifying which can lead to morphology changes. By applying temperature control on the substrate, one can overcome the effect of temperature gradients due to different drop sizes and tailor the dissolution behavior.

Example 7—X-Ray Diffraction

X-ray diffraction was performed on the dosage forms to confirm the physical nature of naproxen. The drops were loaded onto glass sample holders and data collection was performed using CuKα radiation from a Rigaku Smart Lab diffractometer (The Woodlands, Tex.) at 40 kV and 20 mV. Measurements were performed in the range of 5-35° 2θ with a scan rate of 4° 2θ/min and a step size of 0.04° using Bragg-Bretano mode. Si peak was used as an external reference standard. Diffractograms of the crystalline drug, PEG 3350 and physical mixture of the drug with the polymer were collected as reference. X-ray diffraction studies showed that the naproxen present in the dosage forms is crystalline and present in the same polymorphic form as the material used in the formulations both in the presence of PEG 3350 which is shown in FIG. 5.

Example 8—Raman Microscopy

A Raman RXN1 Microprobe (Kaiser Optical Systems, MI) was used to analyze the crystal structure of the naproxen-PEG 3350 melt formulations and to build a map of the drop deposits. First the spectra of pure naproxen and PEG 3350 solid dispersions were obtained. Naproxen and PEG 3350 powders were heated above their melting temperatures, to 160° C. and 60° C., respectively. The melts of pure naproxen and pure PEG 3350 were solidified at room temperature and then analyzed to obtain the spectra of pure compounds. The spectra of the melt formulation consisting of 15% naproxen and 85% PEG 3350 were obtained by analyzing the drops of the melt formulation deposited using the dropwise additive manufacturing process. Raman spectra of pure naproxen melt, pure PEG 3350 melt and melt-based drug deposits of NAP-PEG 3350 (15:85) are presented in FIG. 6A, FIG. 6B, and FIG. 6C respectively. The characteristic peaks of pure naproxen and pure PEG 3350 at 760 $cm^{-1}$ and 1280 $cm^{-1}$ are used for the analysis. Raman spectra of the dosage forms confirm that naproxen present in the dosage forms is crystalline, which is in accordance with x-ray diffraction analysis of the same formulation.

Example 9—Raman Mapping

Raman mapping of the dosage forms was created to study the distribution of the drug over the deposited drops. Therefore a large area of the drop, 660 μm×1000 μm was mapped with 100 μm step sizes, and the map was taken in several different areas of the drop The ratio of the characteristic peaks of the drug to polymer were used in building the color intensity map.

The drug distribution throughout the deposited drop is analyzed using Raman mapping employed for the dosage forms. Different areas throughout the drop deposits were analyzed. Color intensity Raman maps with area (660 μm×1000 μm) were built based on the ratio of the characteristic peaks of naproxen and PEG 3350 at 760 $cm^{-1}$ and 1280 $cm^{-1}$, respectively. The small relative intensity differences confirm that naproxen has an even distribution throughout the drop. This finding is in accordance with HPLC analysis conducted on the melt-based formulations, which suggested that the amount of drug recovered from each drop was the same as the amount present in the drug formulation. Raman measurements performed over different areas of the droplet indicated similarly homogenous drug distribution.

Example 10—Hot Stage Microscopy

A Zeiss Axio Imager A2m polarized light microscope (Carl Zeiss Microscopy, LLC, NY) equipped with a Linkam THMS 600 hot-stage (Linkam Scientific Instruments Ltd., Surrey, UK) was used for this study. The naproxen and PEG 3350 were physically mixed in (15:85) weight ratio and heated to 65° C. until completely melted. After a homogeneous melt was formed, it was cooled down to 30° C. and solidification and crystallization follow. The micrographs of the formulations show in crystalline drug present in the formulations. The induction points were determined by recording the temperature of the sample when the first nucleus was observed.

Example 11—Infrared Imaging

A Flir Systems A65 infra red camera is used to monitor the temperature gradient within the naproxen-PEG 3350 drops solidification of melt-deposits. Indeed infra-red camera images of melt-deposits solidifying at room temperature, indicate that there are temperature gradients present within the drops as they are solidifying. Therefore having temperature control on the drug deposits is crucial for achieving consistent drug morphology.

Example 12—Materials and Formulation—Naproxen II

In this example, naproxen is chosen as the model API to form melt formulations with the block copolymer Pluronic F38 with a molecular weight of 4700. Naproxen (NAP) was purchased from Attix Pharmaceuticals (Montreal, QC, Canada). Pluronic F38 was provided by BASF (Florham Park, N.J.). Naproxen and the polymer Pluronic F38 were mixed in (15:85) weight ratio. The mixture is comelted at 65° C. until completely melted. The melt formulation is printed on polymeric films prepared with hydroxypropyl methylcellulose (HPMC) (E50) and PEG 400. HPMC (E50) is purchased from Sigma Aldrich Corporation (St. Louis, Mo.). PEG 400 was provided by The Dow Chemical Co. (Midland, Mich.).

Example 13—Film Preparation

The film is prepared as described in Example 2.

Example 14—Methodology

After deposition of the drops onto the film, the resulting dosage forms were analyzed to determine whether the different formulations would affect the dissolution behavior of the API. The dosage forms were created and analyzed at the same time and thus varying ambient conditions, such as relative humidity, were not impactful on the results.

Example 15—High Performance Liquid Chromatography Experiments

The chemical stability of naproxen under production is checked in a similar approach as in Example 4. The dosage forms were intentionally subjected to 70° C. for 15 min during production and analyzed using HPLC. The HPLC experiments showed that naproxen found in the dosage forms is stable. The amount recovered is the same of the amount present in the dosage forms and no degradation peaks were observed.

Quantification of the drug in the dosage forms was done using an Agilent 1260 infinity high performance liquid chromatography (HPLC) system as described in Example 4. For analysis of the dosage forms, individual drops of naproxen-Pluronic F38 were dissolved in ACN and diluted appropriately to obtain the concentration in the range of the calibration curve.

Example 16—Reproducibility of Dosage Amounts

Different drop sizes are used to produce the dosage forms with target dosage of 15 mg of API as described in Example 6:

The different drop sizes are obtained by changing the pump and printing operating parameters such as nozzle diameter, displacement, volume strokes and rate. The number of drops needed to reach the target amount varied for each printing setting and was determined experimentally before producing the dosage forms. To analyze reproducibility, HPMC-PEG 400 film measuring 2 cm by 2 cm was weighed on an Omega AL-201s balance. Next, a specific number of drops were deposited on the film to reach the target dosage amount. The films were then subjected to room temperature until the deposits solidify. After solidification of the drops, the films were weighed again to determine the total mass of the deposits on the film. The amount of drug was determined by multiplying this mass of solids by the composition of drug in the solution (15%). These results were then used to analyze how consistently and accurately the dosage forms are created.

To demonstrate different drop sizes, two intermediate sizes of nozzles (i.e. with internal diameters of 15 AWG and 17 AWG) are used. The pump settings are determined to achieve consistent drop formation for both formulations using these nozzle sizes. Using the DAMPP system, dosage forms are produced by printing different sizes of drops on HPMC-PEG films as the substrate. The reproducibility of the dosage forms so produced is shown in Table 2. The relative standard deviation (RSD) is less than 2.05%. These RSD values are well within the 5% RSD limit required by the FDA.

TABLE 2

| Formulation | Number of drops printed | Average dosage amount (mg) | RSD (%) |
|---|---|---|---|
| 15% Naproxen | 10 | 15.76 | 0.69% |
| 85% Pluronic | 9 | 16.11 | 2.05% |
| F38 | 7 | 15.12 | 0.08% |
|  | 6 | 13.77 | 0.17% |

Example 17—Dissolution Testing

Dissolution testing was performed on the dosage forms produced with different sizes of drops as described in Example 6. In FIG. 7, the dissolution profiles of the dosage forms with the formulation containing 15% naproxen and 85% Pluronic F38 are shown. Dissolution of 99% dissolution was achieved in one hour and 85% in 33 minutes.

There are slight differences in the dissolution profiles of the dosage forms printed using different drop sizes. This is due to the effect of the cooling temperature gradient within the drops as they are solidifying which can lead to morphology changes. By applying temperature control on the substrate, one can overcome the effect of temperature gradients due to different drop sizes and tailor the dissolution behavior.

Dosage forms with naproxen-PEG 3350 formulation (described in Naproxen-I examples) have a faster dissolution than the dosage forms containing naproxen-Pluronics F38. This is a result of the structural differences between the two polymers. PEG is a polymer of ethylene oxide (EO) and is hydrophilic with a good solubility in water. It is known to enhance dissolution of many drugs that have poor solubility. Pluronic is a triblock copolymer which consists of repeating chains of EO and propylene oxide (PO) in the structure of $EO_x$-$PO_y$-$EO_x$, where x and y are the average number of EO and PO units respectively. Pluronic F38 consists of 80% EO with a structure of $EO_{43}$-$PO_{16}$-$EO_{43}$. Although Pluronic type polymers are amphiphilic with hydrophilic EO and hydrophobic PO units, those with 80% PEO blocks are considered as very hydrophilic block copolymers with high solubility. However the presence of PPO blocks in the Pluronic F38 containing formulation results in a slower release of the drug compared to PEG 3350 containing formulation.

For the naproxen model drug used, the first formulation, which leads to faster dissolution, is favorable but the use of the Pluronic type polymers might be favorable for some other drugs. Pluronic not only increases oral solubility of poorly soluble drugs by its hydrophilic EO side but it can also enhance the oral absorption of selected drugs with its ability to form unimers or micelles. Pluronic type polymers with large PPO blocks can self-assemble into micelles in aqueous environments and the PO core can serve as a 'cargo' for the incorporation of various hydrophobic compounds that exhibit poor solubility, undesired pharmacokinetics and low stability in physiological environment. Unimers of Pluronic block copolymers increase membrane transport and transcellular permeability in intestinal epithelium cells thus inhibit drug efflux systems in intestinal epithelial cells. Overall, Pluronic® block copolymers may be useful in designing formulations to increase bioavailability of select drugs.

Example 18—X-Ray Diffraction

X-ray diffraction was performed on the dosage forms to confirm the physical nature of naproxen using the methodology of Example 7. Diffractograms of the crystalline drug, Pluronic F38 and physical mixture of the drug with the polymers were collected as reference. X-ray diffraction studies showed that the naproxen present in the dosage forms is crystalline and present in the same polymorphic form as the material used in the formulations in the presence of Pluronic F38 which is shown in FIG. 8.

Example 19—Materials and Formulation—Mevastatin

In this example, mevastatin is chosen as the model API to form melt formulations either with the polymer, polyethylene glycol with a molecular weight of 3350. Mevastatin was purchased from Attix Pharmaceuticals (Montreal, QC, Canada). PEG 3350 was provided by The Dow Chemical Co. (Midland, Mich.). Mevastatin and the polymer PEG 3350 were mixed in (15:85) weight ratio. The mixture is comelted at 65° C. until completely melted. The melt formulation is printed on polymeric films prepared with hydroxypropyl methylcellulose (HPMC) (E50) and PEG 400. HPMC (E50) is purchased from Sigma Aldrich Corporation (St. Louis, Mo.). PEG 400 likewise was provided by The Dow Chemical Co. (Midland, Mich.). The films are prepared as described in Example 2.

Example 20—Raman Spectroscopy

After deposition of the drops onto the film, the crystal structure of the mevastatin-PEG 3350 melt formulations were analyzed with a Raman RXN1 Microprobe (Kaiser Optical Systems, MI). First the spectra of pure mevastatin and PEG 3350 solid dispersions were obtained. Mevastatin and PEG 3350 powders were heated above their melting temperatures, to 152° C. and 60° C., respectively. The melts of pure mevastatin and pure PEG 3350 were solidified at room temperature and then analyzed to obtain the spectra of pure compounds. The spectra of the melt formulation consisting of 15% mevastatin and 85% PEG 3350 were obtained by analyzing the drops of the melt formulation deposited using the dropwise additive manufacturing process. Raman spectra of pure crystalline mevastatin melt, pure PEG 3350 melt and melt-based drug deposits of mevastatin-PEG 3350 (15:85) are presented in FIG. 9A, FIG. 9B, and FIG. 9C respectively. Raman spectra of the dosage forms confirm that mevastatin present in the dosage forms is crystalline.

Example 21—Materials and Formulation—Celecoxib

In this study, celecoxib (CEL) is chosen as the model API to form melt formulations with the surfactant, gelucire 44/14 (Lauroyl macrogol-32 glycerides EP). Celecoxib is purchased from ChemShuttle (Union City, Calif.). Gelucire 44/14 is provided by Gattefosse (Paramus, N.J.). Celecoxib and gelucire 44/14 are mixed in (10:90) weight ratio. The mixture is comelted at 70° C. until completely melted. The melt formulation is printed both onto inert tablets and onto polymeric films prepared with hydroxypropyl methylcellulose (HPMC) (E50). The inert tablets are provided by GlaxoSmithKline (Collegeville, Pa.). HPMC (E50) is purchased from Sigma Aldrich Corporation (St. Louis, Mo.). HPMC films are prepared as described in Example 4, but this time by dissolving 1 g HPMC powder (E50) is dissolved in 20 ml water.

Example 22—Methodology

After deposition of the drops onto the film, the resulting dosage forms were analyzed for solid-state characteristics, self-emulsifying behavior of the formulation and dissolution behavior of the API. The dosage forms were created and analyzed immediately and thus varying ambient conditions, such as relative humidity, were not impactful on the results.

Example 23—Reproducibility of Dosage Amounts

In this study, dosage forms are produced with target dosage of 1.5 mg of API. Each dosage form consists of a single drop containing the target dosing. The drop size can be altered by changing the pump and printing operating parameters such as nozzle diameter, displacement, volume strokes and rate. In addition, by changing the number of drops in a single dose, one can increase the dosage amount. The reproducibility is analyzed both gravimetrically and through image analysis. To analyze reproducibility gravimetrically, substrates are weighed on an Omega AL-201s balance. Next, a specific number of drops are deposited on the substrate to reach the target dosage amount. The dosage forms are then subjected to room temperature until the deposits solidify. After solidification of the drops, the substrates are weighed again to determine the total mass of the deposits on the film. The amount of drug is determined by multiplying this mass of solids by the composition of drug in the solution (10%). These results are then used to analyze how consistently and accurately the dosage forms are created.

Dosage forms are produced using the nozzle with internal diameter of 1.150 mm, pump displacement of 2.5, pump volume stroke of 1 and pump rate of 500. The reproducibility of the dosage forms produced is shown in Table 3. Each dosage form contains 1 drop, and 5 dosage forms are used for the reproducibility calculations. The relative standard deviation (RSD) is less than 3%. These RSD values are well within the 5% RSD limit required by the FDA. The images are recorded via the online imaging system, after the drops are ejected through the nozzle.

TABLE 3

| Formulation | Average dosage amount (mg) | RSD (%) |
| --- | --- | --- |
| 10% celecoxib 90% gelucire 44/14 | 1.58 | 2.64% |

Example 24—Raman Microscopy

A Thermo Scientific DRX Raman Microscope equipped with a 532 nm laser is used to analyze the solid state form of the drug present in the melt formulations. First, the spectra of pure crystalline celecoxib and gelucire 44/14 solid dispersion are obtained. Pure celecoxib and pure gelucire 44/14 are analyzed to obtain the spectra of pure compounds. The spectra of the melt formulation consisting of 10% celecoxib and 90% gelucire 44/14 are obtained by analyzing the drops of the melt formulation deposited using the dropwise additive manufacturing process.

Celecoxib is a rapid crystallizer and its crystallization is shown to be inhibited by the presence of polymers such as HPMC in the solid state. The form of celecoxib in the dosage forms is analyzed with a Raman microscope to investigate the effect of gelucire on crystallization of celecoxib within the deposits. Raman spectra of melt-based drug deposits of 90% gelucire and 10% celecoxib, pure gelucire and pure crystalline celecoxib are presented in FIG. 10A, FIG. 10B, and FIG. 10C respectively. The grey bands clearly show the differences in the peaks of crystalline drug and drug peaks found in the dosage forms. These differences in the peak position, intensity and width are compared with reference spectra of amorphous and crystalline celecoxib from the literature and it is concluded that the celecoxib found in the dosage forms is in the amorphous form.

In FIG. 10, the crystalline spectrum has a double peak at 1614 cm$^{-1}$ with a slight shoulder at 1599 cm$^{-1}$, whereas the spectrum of the dosage form has a double peak with distinct maxima at 1616 cm$^{-1}$ and 1597 cm$^{-1}$. Likewise, the spectrum of the dosage form contains a double peak with distinct maxima at 1185 and 1200 cm$^{-1}$ whereas the spectrum of crystalline celecoxib contains a double peak with a maximum at 1192 cm$^{-1}$ and a shoulder at 1201 cm$^{-1}$. These differences in the spectra are consistent with the reported amorphous and crystalline celecoxib spectra.

Example 25—X-Ray Diffraction

X-ray analysis was performed to ascertain the form of the drug in the formulation. The samples were analyzed using a Rigaku Smartlab diffractometer (The Woodlands, Tex.) with CuK$_\alpha$ radiation source and a D/tex ultra-detector. The voltage and current were 40 kV and 44 mA respectively and the range of data collection was from 5 to 400 2θ at scan speed of 10°/min and a step size of 0.04°.

The crystallinity of the dosage forms is further analyzed with X-ray diffraction. The XRD spectra of melt-based drug deposits of self-emulsifying drug delivery systems ("SEDDS") formulation with 90% gelucire and 10% celecoxib, pure gelucire and pure crystalline celecoxib are presented in FIG. 11. Crystalline peaks of celecoxib were not observed in the dosage forms produced with the SEDDS formulation. Along with the Raman analysis, the presence of amorphous celecoxib in the dosage forms is thus demonstrated.

Example 26—Nanoparticle Tracking Analysis (NTA)

NTA was utilized to characterize the solution formed after dissolving the SEDDS formulation containing 1 mg of celecoxib in 160 mL of distilled water. The emulsion that was formed after dissolution of the dosage form was analyzed using the Nanosight LM10 (Malvern instruments, Massachusetts) instrument. The light source of the instrument was a green laser of 532 nm wavelength. The light scattered by the particles was visualized using a 20× magnification objective which was attached to a CMOS camera. Particle size distribution analysis was performed by acquiring a 30 sec video and processing it using the Nanosight NTA 3.0 software.

The formulation displays spontaneous self-emulsifying characteristics upon dilution in aqueous media. In order to further analyze the resulting emulsion, a technique called nanoparticle tracking analysis (NTA) is used. NTA utilizes the properties of both light scattering and Brownian motion in order to obtain the particle size distribution of nanoparticles in solution. The size distribution profile of emulsion droplets obtained from the SEDDS containing of 10% celecoxib and 90% gelucire is presented in FIG. 12. NTA also enables visualization and recording of particles, which is not shown. White dots correspond to the particles that are observed in contrast to the black background. Using the software, the mean particle size is found as 160.76 nm. Thus, the celecoxib-gelucire (10:90) formulation results in the formation of a submicron spontaneous emulsion.

Example 27—Dissolution Testing and High Performance Liquid Chromatography Experiments Dissolution testing of crystalline celecoxib and the SEDDS formulation was performed in 900 mL of pH 6.8 10 mM phosphate buffer in a USP-I paddle dissolution apparatus. Experiments were performed at 100 rpm at 37° C. Aliquots were taken from the dissolution vessels and filtered through a 1 μm glass filter. The volume of the sampled aliquots was replenished using fresh dissolution medium. The filtered samples were then analyzed using an Agilent 1100 series HPLC (Santa Clara, Calif.) fitted with a UV detector. Samples were run through a Kinetex 2.6μ C$_{18}$ column (150×3.0 mm) at a flow rate of 0.5 mL and a column temperature of 50° C. The mobile phase consisted of 30% pH 3.5 water adjusted using phosphoric acid and 70% methanol. The injection volume was 20 μL and the absorbance was monitored at the wavelength of 250 nm. Each experiment was performed in triplicate.

Dissolution testing was performed on the dosage forms manufactured using the self-emulsifying formulation. In FIG. 13, the dissolution profiles of the dosage forms are compared with that of crystalline celecoxib. The crystalline solubility limit of celecoxib has been reported to be in the range of 1.1 to 1.5 μg/ml. The solubility limits are shown as the dotted black lines, which correspond to a release of 63-85% of the SEDDS dosage forms. The solubility between two limits is shown with the grey band in the figure. For the SEDDS formulation, a dissolution of 70% of the dose is reached in 10 min. The dissolution reaches a plateau at around 75% dissolution which indicates that the crystalline solubility limit is reached and increasing the testing time does not affect the release profile. On the other hand, the crystalline celecoxib reaches only 22% release in 2 hours under the same conditions. Thus, the SEDDS formulation promotes rapid dissolution of celecoxib up to the concentration equivalent to the crystalline solubility.

Although celecoxib in the SEDDS is in amorphous form, during dissolution testing it does not exceed the crystalline solubility. This is due to rapid crystallization of celecoxib when dissolved in the buffer solution. When the deposits are dissolved in buffer solution, the celecoxib within the deposits recrystallizes after 5 min. Optical microscopy images of celecoxib crystals in buffer solution following dissolution of the SEDDS formulation confirm recrystallization in solution.

Example 28—Drop Reproducibility

To demonstrate the reproducibility of the drops, a melt of PEG 3350 is printed using the 15 AWG (American wire gauge) nozzle, 2.5 displacement, 1200 RPM, and volume strokes of 1. The average volume of the drops printed with this formulation and printing settings is 13.70:L with a relative standard deviation (RSD) of 1.59%.

Example 29—Materials and Formulation—Acetaminophen I

In this example, micronized acetaminophen (paracetamol) was chosen as the model API to create suspension formulations with NEOBEE® 895 (96% glycerol trioctanoate, 4% glycerol tridecanoate, mass basis), a purified vegetable oil. Micronized acetaminophen purchased from Mallinckrodt Pharmaceuticals (Item Code 0422: Acetaminophen USP/Paracetamol Ph Eur Micronized) was provided by Prof Carl Wassgren (Purdue University, West Lafayette, Ind.). NEOBEE® 895 was provided by Stepan Company (Millsdale, Ill.). Micronized acetaminophen and NEOBEE® 895 were mixed in such quantities as to create a suspension consisting of 32% acetaminophen by mass, corresponding to a suspension of 25% acetaminophen by volume. The suspension formulation was printed into 0.6 cm$^3$ centrifuge vials purchased from Fisher Scientific. The intended dosage form employs size 1 (or smaller) gelatin capsules, the orifice of which is closely approximated in diameter by that of a 0.6 cm$^3$ centrifuge vial.

Example 30—API Powder Characterization

In order to formulate suspensions, accommodate fluid rheological constraints and quantify effects related to particle morphology, three dry powder characterization techniques were employed. Skeletal (true) density of the particles was determined by helium gas pycnometry, bulk density was determined using a standard tapped density tester, and particle morphology was assayed by static image analysis.

Example 31—API Particle Skeletal (True) Density

The AccuPyc II 1340 Gas Displacement Pycnometry System (Micromeritics Instrument Corporation, Norcross, Ga.) was used to determine the skeletal density of the micronized acetaminophen powder. The AccuPyc II 1340 instrument determines the volume occupied by powder sample, and with knowledge of the sample mass (determined on a XS105 DualRange (Mettler Toledo, Switzerland)) the skeletal density is calculated; purge cycles function to clear the chamber of residual volatile species and occur prior to the measurement cycles. Helium gas was used as the measurement gas, and the following instrument specifications were used in each powder sample: 10 purges (purge fill pressure 19.5 psig), 10 cycles (cycle fill pressure 19.5 psig), pressure equilibration rate 0.0050 psig/min, 3.5 cm$^3$ cell volume. Performed at ambient conditions of 22° C. and 52% relative humidity, the density reported here corresponds to the mean value obtained from measurement of four powder samples. The density of micronized acetaminophen powder was determined to be 1.3285 g/cm$^3$.

Example 32—API Powder Bulk Density

In order to determine the solid volume fractions under which the mixtures of the micronized acetaminophen powder and NEOBEE® 895 would flow as a suspension, bulk density measurements were taken using the 350 Tapped Density Tester (Agilent Technologies, Santa Clara, Calif.), housed in an acoustic cabinet. The test was performed in accordance with ASTM standard D7481-09 (equivalent to USP Method 1) using a 100 mL graduated cylinder with drop height of 14±2 mm at a rate of 300 drops per minute. The mass of the powder sample was determined on a MS8001S NewClassic MF (Mettler Toledo, Switzerland) resulting in a bulk density of 0.36 g/cm$^3$ after 6000 taps, measured at 21.9° C. and 40% relative humidity.

Example 33—API Particle Size and Shape

The micronized acetaminophen particle size distribution was obtained using the Malvern Morphologi G3-ID, which employs static image analysis to determine morphology. Powder samples of 7 mm$^3$ were obtained using a standard scoop, transferred to the attached dispersion unit (operated with 0.1 bar pressure and 60 second dispersion cycle) and analyzed at 20× magnification. The micronized acetaminophen was found to have a Sauter mean diameter of 22.05 μm and $d_{90}$ of 75.29 μm.

Example 34—Methodology

In order to generate homogeneous suspensions, the micronized acetaminophen and NEOBEE® 895 were mixed and subsequently homogenized for 30 seconds with an MX-S vortex mixer (Scilogex, Berlin, Conn.), then allowed to equilibrate for 24 hours. After passage of 24 hours, the suspensions were homogenized again for 30 seconds prior to printing. After deposition of the drops into the 0.6 cm$^3$ centrifuge vials, the vials were closed to the atmosphere and the suspension mass quantified on an Omega AL-201S balance.

Example 35—Analysis of Dosage Amounts

Generation of reproducible drops was achieved by tuning pump parameters for a 17 AWG nozzle size; 10 drops were dispensed into each conical vial, the vial sealed and subsequently weighed. The mass of API delivered was calculated from the volume fraction of API in the suspension and the API's skeletal density. The micronized acetaminophen-NEOBEE® 895 suspension produced acetaminophen dosage amounts of 34.0 mg with RSD 1.87%.

Example 36—Materials and Formulation—Acetaminophen II

In this example, semi-fine acetaminophen (paracetamol) was chosen as the model API to create suspension formulations with NEOBEE® 895 (96% glycerol trioctanoate, 4% glycerol tridecanoate, mass basis), a purified vegetable oil. Micronized acetaminophen purchased from Mallinckrodt Pharmaceuticals (Item Code 0081: Acetaminophen USP/Paracetamol Ph Eur Semi-Fine Powder) was provided by Prof. Carl Wassgren (Purdue University, West Lafayette, Ind.). NEOBEE® 895 was provided by Stepan Company (Millsdale, Ill.). Semi-fine acetaminophen and NEOBEE® 895 were mixed in such quantities as to create a suspension consisting of 42% acetaminophen by mass, corresponding to a suspension of 34% acetaminophen by volume. The suspension formulation was printed into 0.6 cm$^3$ centrifuge vials purchased from Fisher Scientific. The intended dosage form employs size 1 (or smaller) gelatin capsules, the orifice of which is closely approximated in diameter by that of a 0.6 cm$^3$ centrifuge vial.

Example 37—API Particle Skeletal (True) Density

Skeletal density was determined by the same procedure described in Example 31; testing was performed at ambient conditions of 22° C. and 51% relative humidity. The density reported here corresponds to the mean value obtained from measurement of four powder samples; the density of semi-fine acetaminophen powder was determined to be 1.3274 g/cm$^3$.

Example 38—API Powder Bulk Density

Bulk density was determined by the same procedure described in Example 32; testing was performed at 22.1° C. and 45% relative humidity. Bulk density was found to be 0.46 g/cm$^3$ after 8000 taps.

Example 39—API Particle Size and Shape

Particle morphology was determined in the same manner described in Example 33, but at a magnification of 5×. The semi-fine acetaminophen was found to have a Sauter mean diameter of 47.66 µm and $d_{90}$ of 208.8 µm.

Example 40—Methodology

In order to generate homogeneous suspensions, the semi-fine acetaminophen and NEOBEE® 895 were mixed and subsequently homogenized for 30 seconds with an MX-S vortex mixer (Scilogex, Berlin, Conn.), then allowed to equilibrate for 24 hours. After passage of 24 hours, the suspensions were homogenized again for 30 seconds prior to printing. After deposition of the drops into the 0.6 cm$^3$ centrifuge vials, the vials were closed to the atmosphere and the suspension mass quantified on an Omega AL-201S balance.

Example 41—Analysis of Dosage Amounts

Generation of reproducible drops was achieved by tuning pump parameters for a 17 AWG nozzle size; 10 drops were dispensed into each conical vial, the vial sealed and subsequently weighed. The mass of API delivered was calculated from the volume fraction of API in the suspension and the API's skeletal density. The semi-fine acetaminophen-NEOBEE® 895 suspension produced acetaminophen dosage amounts of 46.6 mg with RSD 2.53%.

Example 42—Materials and Formulation—Mefenamic Acid

In this example, mefenamic acid was chosen as the model API to create suspension formulations with NEOBEE® 895 (96% glycerol trioctanoate, 4% glycerol tridecanoate, mass basis), a purified vegetable oil. Mefenamic acid (Product Number M1782: Mefenamic Acid) was purchased from Tokyo Chemical Industry America. (Philadelphia, Pa.). NEOBEE® 895 was provided by Stepan Company (Millsdale, Ill.). Mefenamic acid and NEOBEE® 895 were mixed in such quantities as to create a suspension consisting of 56% mefenamic acid by mass, corresponding to a suspension of 49% mefenamic acid by volume. The suspension formulation was printed into 0.6 cm$^3$ centrifuge vials purchased from Fisher Scientific. The intended dosage form employs size 1 (or smaller) gelatin capsules, the orifice of which is closely approximated in diameter by that of a 0.6 cm$^3$ centrifuge vial.

Example 43—API Particle Skeletal (True) Density

Skeletal density was determined by the same procedure described in Example 31; testing was performed at ambient conditions of 22.6° C. and 53% relative humidity. The density reported here corresponds to the mean value obtained from measurement of four powder samples; the density of mefenamic acid powder was determined to be 1.2706 g/cm$^3$.

Example 44—API Powder Bulk Density

Bulk density was determined by the same procedure described in Example 32; testing was performed at 22.1° C. and 45% relative humidity. Bulk density was found to be 0.7423 g/cm$^3$ after 6000 taps.

Example 45—API Particle Size and Shape

Particle morphology was determined in the same manner described in Example 33, but at a magnification of 5×. The mefenamic acid powder was found to have a Sauter mean diameter of 88.83 µm and $d_{90}$ of 400.5 µm.

Example 46—Methodology

In order to generate homogeneous suspensions, the mefenamic acid and NEOBEE® 895 were mixed and subsequently homogenized for 30 seconds with an MX-S vortex mixer (Scilogex, Berlin, Conn.), then allowed to equilibrate for 24 hours. After passage of 24 hours, the suspensions were homogenized again for 30 seconds prior to printing. After deposition of the drops into the 0.6 cm$^3$ centrifuge vials, the vials were closed to the atmosphere and the suspension mass quantified on an Omega AL-201S balance.

Example 47—Analysis of Dosage Amounts

Generation of reproducible drops was achieved by tuning pump parameters for a 17 AWG nozzle size; 10 drops were dispensed into each conical vial, the vial sealed and subsequently weighed. The mass of API delivered was calculated from the volume fraction of API in the suspension and the API's skeletal density. The mefenamic acid-NEOBEE® 895 suspension produced mefenamic acid dosage amounts of 59.5 mg with RSD 1.46%.

Example 48—Materials and Formulation—Acetaminophen II

In this example, micronized acetaminophen (paracetamol) was chosen as the model API to create suspension formulations with NEOBEE® 895 (96% glycerol trioctanoate, 4% glycerol tridecanoate, mass basis), a purified vegetable oil. Micronized acetaminophen purchased from Mallinckrodt Pharmaceuticals (Item Code 0422: Acetaminophen USP/Paracetamol Ph Eur Micronized) was provided by Prof Carl Wassgren (Purdue University, West Lafayette, Ind.). Dow Corning® Q7-9180 Silicone Fluid (Hexamethyldisiloxane, 99.9%) was purchased from Univar USA (Downers Grove, Ill.). Micronized acetaminophen and Dow Corning® Q7-9180 Silicone Fluid were mixed in such quantities as to create a suspension consisting of 16% acetaminophen by mass, corresponding to a suspension of 10% acetaminophen by volume. The suspension formulation was printed into 0.6 cm$^3$ centrifuge vials purchased from Fisher Scientific. The intended dosage form employs size 1 (or smaller) gelatin capsules, the orifice of which is closely approximated in diameter by that of a 0.6 cm$^3$ centrifuge vial.

Example 49—API Particle Skeletal (True) Density

Skeletal density was determined by the same procedure described in Example 31.

Example 50—API Powder Bulk Density

Bulk density was determined by the same procedure described in Example 32.

Example 51—API Particle Size and Shape

Particle morphology was determined in the same manner described in Example 33.

Example 52—Methodology

In order to generate homogeneous suspensions, the micronized acetaminophen and Dow Corning® Q7-9180 Silicone Fluid were mixed and subsequently homogenized for 30 seconds with an MX-S vortex mixer (Scilogex, Berlin, Conn.), then allowed to equilibrate for 24 hours. After passage of 24 hours, the suspensions were homogenized again for 30 seconds prior to printing. After deposition of the drops into the 0.6 $cm^3$ centrifuge vials, the vials were closed to the atmosphere and the suspension mass quantified on an Omega AL-201S balance.

Example 53—Analysis of Dosage Amounts

Generation of reproducible drops was achieved by tuning pump parameters for a 17 AWG nozzle size; 10 drops were dispensed into each conical vial, the hexamethyldisiloxane evaporated, the vial sealed and subsequently weighed. The micronized acetaminophen-Dow Corning® Q7-9180 Silicone Fluid suspension produced acetaminophen dosage amounts of 13.6 mg with RSD 2.60%.

We claim:

1. An active ingredient delivery system comprising:
   a. a fluid reservoir for receiving a fluid therein;
   b. a fluid-delivery apparatus comprising a pump, a fluid-dispensing device comprising a first end and a second end, and a heated air tube extending between a housing of the pump and the fluid dispensing device, wherein the first end of the fluid-dispensing device is in fluid communication with the fluid reservoir via a fluid transfer tube positioned inside the heated air tube, and the pump is positioned to transfer the fluid from the reservoir, through the pump, and to and through the fluid-dispensing device;
   c. a real-time drop-imaging and measurement device; and
   d. a substrate holder positioned below the second end of the fluid dispensing device, the substrate holder comprising a heating element, a cooler, and a stage configured to position a substrate thereon to receive the fluid flowing through the second end of the fluid-dispensing device;
   wherein the fluid reservoir contains a fluid suspension comprising an active ingredient and the fluid-dispensing device comprises a nozzle.

2. The system of claim 1, wherein the fluid suspension comprises one or more of an excipient and a colloid.

3. The system of claim 1, wherein the active ingredient is a pharmaceutically active ingredient.

4. The system of claim 1, wherein at least one of the reservoir, the nozzle, and/or the pump is/are under temperature control.

5. The system of claim 1, wherein the pump is a positive displacement pump and further comprises a controller for adjusting pump parameters.

6. The system of claim 1, wherein at least a portion of the real-time drop-imaging and measurement device is positioned between the second end of the fluid dispensing device and the substrate holder and configured to image the fluid suspension emerging from the second end of the fluid dispensing device as one or more drops and the real-time drop-imaging and measurement device is further configured to measure a volume of the one or more drops.

7. The system of claim 1, wherein the fluid dispensing device is a nozzle, the system further comprising a detector positioned below and transverse the second end of the nozzle, the detector comprising a photosensor and two fiber optic cables mounted on a housing attached to a nozzle assembly, wherein the detector device is configured to send a signal to activate the real-time drop imaging and measurement device when one or more drops of the fluid passes in front of a light beam passing between ends of the two fiber optic cables.

8. The system of claim 7, further comprising a backlight, wherein the backlight is configured so that when one or more drops of the fluid are imaged, light from the backlight is in a field of view of a camera of the real-time drop imaging and measurement device, the camera directed at the one or more drops of the fluid, and wherein said light is perpendicular to the light beam from the two fiber optic cables.

9. The system of claim 1, further comprising an analytical instrument configured to analyze active ingredients of the substrate, and wherein the analytical instrument is selected from one or more of the group consisting of a Raman spectrometer, an infrared spectrometer, an x-ray powder diffractometer, a differential scanning calorimeter, a thermal gravimetric analyzer, a mass spectrometer, a gravimetric instrument, a dissolution apparatus, a particle size measurement instrument, a gas displacement pycnometer, a tapped density tester, and a chromatography instrument.

10. A method for delivering an active ingredient to a substrate, comprising the steps of:
   a. preparing a fluid suspension comprising an excipient and pharmaceutically active ingredient;
   b. transporting the fluid suspension, using a pump, through the fluid transfer tube, through the pump, and into the nozzle, wherein the fluid transfer tube is positioned inside a heated air tube extending between a housing of the pump and the nozzle;
   c. ejecting the prepared fluid suspension through a nozzle onto a substrate positioned below the nozzle on a substrate holder comprising a heating element, a cooler, and a stage, wherein the nozzle creates one or more drops of the fluid suspension; and
   d. measuring the volume of the one or more drops of the fluid suspension using a real-time drop-imaging and measurement device.

11. The method of claim 10, wherein:
   the excipient comprises a polymer, and
   the fluid suspension is heated within a fluid reservoir to a temperature greater than a melting temperature of the polymer, the fluid reservoir in fluid communication with the nozzle via the fluid transfer tube.

12. The method of claim 10, wherein a diameter of the nozzle is adjusted so that the one or more drops have a volume between about one microliter and about 35 microliters per drop.

13. The method of claim 10, wherein a volume of the one or more drops is measured after the one or more drops exit the nozzle.

14. The method of claim 10, further comprising the step of analyzing the pharmaceutically active ingredient on the substrate.

15. A method for preparing a microdose of an active pharmaceutical ingredient comprising:
  a. preparing a fluid suspension comprising an excipient and one or more active pharmaceutical ingredients;
  b. using a pump, transporting the prepared fluid through the pump and a fluid transfer tube positioned inside a heated air tube, the fluid transfer tube and heated air tube extending between a housing of the pump and a nozzle, and ejecting the prepared fluid through the nozzle onto a substrate holder positioned below the nozzle, wherein the nozzle creates one or more drops of the fluid and wherein the substrate holder comprises a stage, a substrate, a heating element and a cooler;
  c. measuring the volume of the one or more drops; and
  d. processing the one or more drops to provide a microdose of the one or more active pharmaceutical ingredients.

16. The method of claim 15, wherein the excipient comprises at least one of a polymer, lipid, or surfactant, and a positive displacement pump is used to eject the fluid suspension.

17. The method of claim 15, wherein the substrate is selected from the group consisting of a dermal patch, a sublingual product, a buccal product, an injectable, a syringe, a tablet, a film strip, a capsule, and a vial.

18. The method of claim 15, wherein the processing comprises reducing a temperature of the substrate so that the fluid suspension hardens.

* * * * *